United States Patent [19]

Guglielmetti

[11] Patent Number: 4,508,784
[45] Date of Patent: Apr. 2, 1985

[54] 4-STYRYL-4'-VINYLBIPHENYLS, THE PRODUCTION THEREOF AND USE THEREOF AS FLUORESCENT

[75] Inventor: Leonardo Guglielmetti, Bottmingen, Switzerland

[73] Assignee: Ciba Geigy Corporation, Ardsley, N.Y.

[21] Appl. No.: 572,973

[22] Filed: Jan. 23, 1984

Related U.S. Application Data

[63] Continuation of Ser. No. 327,665, Dec. 7, 1981, abandoned.

[30] Foreign Application Priority Data

Dec. 12, 1980 [CH] Switzerland ............... 9192/80

[51] Int. Cl.$^3$ ............................ B32B 9/04
[52] U.S. Cl. ..................... 252/301.21; 8/648; 252/301.27; 260/465 R; 260/465 D; 260/465 G; 427/158; 428/480; 560/51; 560/81; 585/25; 585/469
[58] Field of Search ............... 427/158, 157; 252/301.21, 301.27, 301.28; 260/453 R, 456 R, 456 A, 456 P, 465 C, 245.6, 465 R, 465 G, 465 D; 585/469, 25; 428/411, 480; 8/648; 560/81, 51

[56] References Cited

U.S. PATENT DOCUMENTS 3,984,399 10/1976 Weber et al. ............... 8/648
4,118,560 10/1978 Weber ............... 427/158 X
4,147,648 4/1979 Gunter et al. ............... 427/158 X Primary Examiner—S. L. Childs
Attorney, Agent, or Firm—Roberts: Edward McC.

[57] ABSTRACT

The invention relates to novel 4-styryl-4'-vinylbiphenyls of the formula

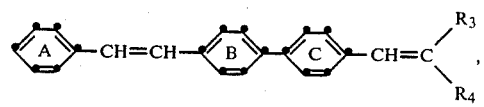

wherein the benzene rings A, B and C can carry non-chromophoric substituents and $R_3$ is a second order non-chromophoric substituent, and $R_4$ is hydrogen or a non-chromophoric substituent which cannot be a second order substituent, and also a process for obtaining them. These novel compounds can be used as fluorescent whitening agents for treating organic material of high molecular weight, preferably textile material, most preferably polyester fibres. The invention also discloses novel intermediates of the formula

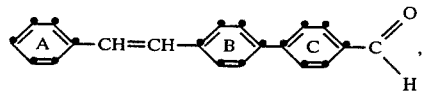

wherein A, B and C are as defined above, which are formed during the production of the novel 4-styryl-4'-vinylbiphenyls, and also a process for obtaining them.

24 Claims, No Drawings

4-STYRYL-4'-VINYLBIPHENYLS, THE PRODUCTION THEREOF AND USE THEREOF AS FLUORESCENT

This application is a continuation of application Ser. No. 327,665, filed 12/7/81 abandoned.

The present invention relates to novel 4-styryl-4'-vinylbiphenyls, to the production thereof, and to the use thereof for whitening synthetic, regenerated, and natural high-molecular organic material. The invention also relates to novel 4-styrylbiphenylaldehydes and 4-vinylbiphenylaldehydes obtained as intermediates in the production of the 4-styryl-4'-vinylbiphenyls of this invention, and to the production of these intermediates.

Vinyl-substituted fluorescent whitening agents, viz. 4,4'-bis-vinylstilbenes, are disclosed in German Offenlegungsschrift Ser. No. 26 02 750. It is the object of the present invention to provide novel useful fluorescent whitener compounds with which particularly good white effects are obtained and which have very good exhaust and lightfastness properties.

Surprisingly, it has been found that 4-styryl-4'-vinylbiphenyls have these properties and accordingly are most suitable for the purpose of the invention. The novel fluorescent whitening agents are also highly productive.

The 4-styryl-4'-vinylbiphenyls of this invention have the formula

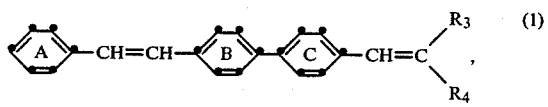

wherein the benzene rings A, B and C can carry non-chromophoric substituents and $R_3$ is a second order non-chromophoric substituent, and $R_4$ is hydrogen or a non-chromophoric substituent which cannot be a second order substituent.

Suitable non-chromophoric substituents in compounds of the formula (1) are, in particular, those which are customary in the field of fluorescent whitening agents. Examples of such substituents are: unsubstituted or substituted alkyl or alkoxy, alkenyl, cycloalkyl, aryl, aralkyl, alkoxycarbonyl; unsubstituted or substituted aminocarbonyl, cyano, alkylsulfonyl, alkoxysulfonyl; unsubstituted or substituted aminosulfonyl, acyl, acylamino, hydroxy, aryloxy, aralkoxy, alkenyloxy, aryloxycarbonyl, aralkyloxycarbonyl, carboxy, sulfo, acyloxy or trifluoromethyl.

The term "aryl" will preferably be understood as meaning aromatic mono- or polynuclear carbocyclic ring systems, e.g. naphthyl(1) or naphthyl(2), preferably phenyl. In composite groups (e.g. aryloxy, aralkyl, aralkoxy etc.), the same definition applies to aryl.

Examples of non-chromophoric substituents of alkyl or alkoxy groups are: hydroxyl, alkoxy, alkoxyalkoxy, hydroxyalkoxy, halogen, cyano, aryl (especially phenyl), sulfo, carboxyl, carbalkoxy, aminocarbonyl.

If aryl groups (or aryl moieties of composite radicals), especially phenyl groups (or phenyl moieties of composite radicals such as phenoxy, phenylalkyl, phenylsulfonyl etc.) are substituted, they preferably carry one or two substituents selected from the group consisting of halogen (especially chlorine), alkyl and/or alkoxy, and also sulfo or carboxyl and derivatives thereof, cyano, amino, alkylamino, dialkylamino and acyl. Preferred substituents are chlorine, methyl and methoxy, three of which can also be present in the ring.

Halogen is preferably fluorine, chlorine or bromine, with chlorine being most preferred. Acyl is preferably alkylcarbonyl, alkylsulfonyl, and phenylsulfonyl which can be substituted by alkyl, alkoxy or halogen.

Alkyl and alkoxy groups by themselves or as moieties of composite groups usually contain 1 to 8, preferably 1 to 6, and, most preferably, 1 to 4 carbon atoms. Cycloalkyl preferably contains 5 to 6 carbon atoms in the ring. Alkenyl groups preferably contain 2 to 6, most preferably 3 or 4, carbon atoms. Alkyl moieties of carboxylic acid ester or carboxamide groups or of sulfonamide groups preferably contain 1 to 8 carbon atoms.

Second order non-chromophoric groups are the electron attracting (withdrawing) substituents known in organic chemistry, e.g. acyl radicals of organic carboxylic or sulfonic acids, cyano, trifluoromethyl, the carboxyl group and the sulfo group and the functional derivatives thereof e.g. the salts, esters and amides thereof, as well as derivatives of radicals of oxyphosphorous compounds.

By alkoxy are also meant groups of the formula —$(OCH_2—CH_2—)_n$—OR, wherein R is hydrogen or $C_1$–$C_4$alkyl and n is an integer from 1 to 6. As further substituents, there may also be mentioned those of the formula —$CH_2$—$CH_2$—$O)_n(C_1$–$C_4$alkyl), wherein n is as defined above.

Within the scope of the compounds of formula (1), interesting compounds are those of the formula

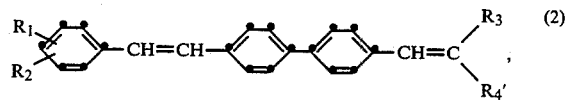

wherein
each of $R_1$ and $R_2$ is hydrogen or a non-chromophoric substituent, or both together in the ortho-position complete a fused ring,
$R_3$ is a second order non-chromophoric substituent and $R_4'$ is hydrogen or alkyl or alkenyl, each unsubstituted or substituted by non-chromophoric groups.

Suitable non-chromophoric substituents $R_1$ and $R_2$ are preferably those mentioned above. Suitable fused rings which can be completed by $R_1$ and $R_2$ taken together are preferably benzene, naphthalene, cyclohexene or cyclopentene rings, or both radicals together form the methylenedioxy, ethylenedioxy or oxymethylene-oxymethylene radical. Preferred non-chromophoric substituents of alkyl groups ($R_4'$) are mentioned above. The same substituents can also carry alkenyl groups. Second order non-chromophoric substituents have also previously been exemplified under formula (1).

Preferred compounds are those of the formula

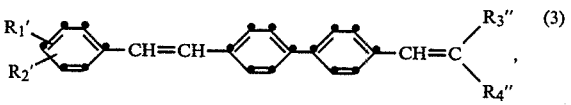

wherein $R_1'$ is hydrogen, halogen, alkyl, alkoxy or alkylsulfonyl, each unsubstituted or substituted by non-chromophoric groups; phenyl, phenylalkyl or phenylsulfonyl, phenoxy or phenylalkoxy, each unsubstituted or substituted by non-chromophoric groups; or is cyano, a group of the formula —COOY$_1$, —CONY$_1$Y$_2$ or —SO$_2$NY$_1$Y$_2$, wherein each of Y$_1$ and Y$_2$ independently is hydrogen, alkenyl, propargyl, cycloalkyl containing 5 or 6 ring carbon atoms, or is alkyl, phenyl or phenylalkyl, each unsubstituted or substituted by non-chromophoric groups; or Y$_1$ and Y$_2$, together with the nitrogen atom to which they are attached, are a 5- or 6-membered saturated heterocyclic ring which can additionally contain 1 or 2 hetero-atoms as ring members and can also be substituted by alkyl groups; or wherein Y$_1$ in the group —COOY$_1$ can also additionally be a salt-forming cation; or R$_1$' is a group of the formula

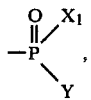

wherein each of X$_1$ and Y independently of the other is halogen, alkyl, alkenyl, phenyl, phenylalkyl, hydroxy, alkoxy, phenylalkoxy, cycloalkoxy, phenoxy, amino, mono- or dialkylamino, phenylalkylamino, acylamino, phenylamino, cycloalkylamino, morpholino, piperidino or pyrrolidino; or R$_1$' together with R$_2$' in the ortho-position are the radical of the formula —CH=CH—CH=CH—, —O—CH$_2$—O— or —O—CH$_2$—CH$_2$—O—; R$_2$' is hydrogen, halogen, or alkyl or alkoxy, each unsubstituted or substituted by non-chromophoric groups; or R$_2$' together with R$_1$' in the ortho-position are the radical of the formula —CH=CH—CH=CH—, —O—CH$_2$—O— or —O—CH$_2$—CH$_2$—O—; R$_3$'' is alkylsulfonyl, phenylsulfonyl, alkoxysulfonyl, cyano, trifluoromethyl, sulfo, a group of the formula —COOY$_1$, —CONY$_1$Y$_2$ or —SO$_2$NY$_1$Y$_2$, wherein Y$_1$ and Y$_2$ are as defined above; or is a group of the formula

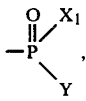

wherein X$_1$ and Y are as defined above; and R$_4$'' is hydrogen or alkyl which is unsubstituted or substituted by non-chromophoric groups.

Examples of non-chromophoric substituents for alkyl groups (and thus also for alkoxy and alkylsulfonyl groups) and for phenyl radicals and groups containing phenyl radicals, have previously been listed under formula (1).

If 5- or 6-membered saturated heterocyclic rings (Y$_1$+Y$_2$) contain additional hetero-atoms in the ring, such hetero-atoms can preferably be 1 or 2 nitrogen, oxygen and/or sulfur atoms. Preferred hetero-cyclic rings which may be formed by Y$_1$ and Y$_2$ together with the nitrogen atom to which they are attached, are the piperidine, piperazine, morpholine, thiomorpholine, pyrrolidine, imidazolidine and oxazolidine ring. Such heterocyclic rings can be additionally substituted by 1 or 2 alkyl groups, preferably those containing 1 to 4 carbon atoms.

A suitable salt-forming cation Y$_1$ is preferably an alkali metal ion (e.g. Na, K), an ammonium ion or a substituted ammonium ion (amine salt ion).

Preferred compounds within the scope of the formula (3) are those of the formula

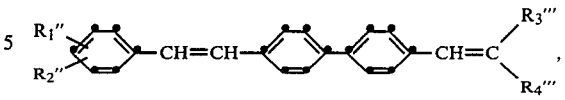

wherein R$_1$'' is hydrogen, halogen, C$_1$–C$_4$alkyl, C$_1$–C$_4$alkoxy, C$_1$–C$_4$alkylsulfonyl, cyano, or phenyl or phenylsulfonyl, each unsubstituted or substituted by chlorine, methyl and/or methoxy; or is a group of the formula —COOY$_1$', —CONY$_1$'Y$_2$' or —SO$_2$NY$_1$'Y$_2$', wherein Y$_1$' is hydrogen, C$_1$–C$_8$-alkyl, C$_3$–C$_4$alkenyl, cyclohexyl, C$_2$–C$_4$hydroxyalkyl, C$_3$–C$_6$alkoxyalkyl, a radical of the formula —CH$_2$CH$_2$O)$_n$(C$_1$–C$_4$alkyl), wherein n is an integer from 1 to 6, or is C$_6$–C$_9$phenoxyalkyl, C$_2$–C$_6$carboxyalkyl, C$_3$–C$_6$carbalkoxyalkyl, C$_2$–C$_5$cyanoalkyl, phenyl or benzyl, each unsubstituted or substituted by chlorine, methyl and/or methoxy, or is C$_3$–C$_7$dialkylaminoalkyl or phenethyl; Y$_2$' is hydrogen, C$_1$–C$_4$alkyl, C$_3$–C$_4$alkenyl or C$_2$–C$_4$hydroxyalkyl, or Y$_1$' and Y$_2$', together with the nitrogen atom to which they are attached, are a 5- or 6-membered saturated heterocyclic ring which can additionally contain a further nitrogen or oxygen atom as ring member and which can be substituted by 1 or 2 C$_1$–C$_4$ alkyl groups; or wherein Y$_1$' in the group —COOY$_1$' can additionally be an alkali metal ion or an ammonium ion; or R$_1$'' is a group of the formula

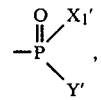

wherein each of X$_1$' and Y' independently of the other is C$_1$–C$_4$alkyl, benzyl, phenyl which is unsubstituted or substituted by chlorine, methyl and/or methoxy; R$_2$'' is hydrogen, halogen or C$_1$–C$_4$-alkyl; R$_3$'' is cyano, C$_1$–C$_4$alkylsulfonyl or a group of the formula —COOY$_1$', —CONY$_1$'Y$_2$', SO$_2$NY$_1$'Y$_2$' or

wherein Y$_1$', Y$_2$', X$_1$' and Y' are as defined above; and R$_4$''' is hydrogen or C$_1$–C$_4$alkyl; and also compounds of the formula

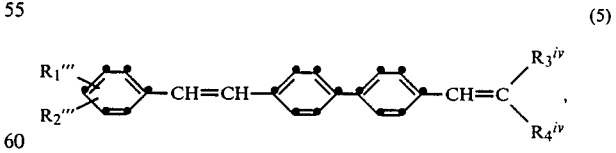

wherein R$_1$''' is halogen, C$_1$–C$_4$alkylsulfonyl, cyano or a group of the formula —COOY$_1$'', wherein Y$_1$'' is C$_1$–C$_8$alkyl, C$_3$–C$_4$alkenyl, C$_2$–C$_4$hydroxyalkyl, C$_3$–C$_6$alkoxyalkyl, a radical of the formula —CH$_2$CH$_2$—O)$_{n'}$(C$_1$–C$_4$-alkyl), wherein n' is an integer from 1 to 4, or is C$_2$–C$_6$carboxyalkyl, C$_3$–C$_6$carbalkoxyalkyl or C$_2$–C$_5$cyanoalkyl; or is a group of the formula

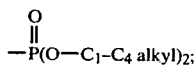

$R_2'''$ is hydrogen or halogen; $R_3^{Iv}$ is $C_1$-$C_4$-alkylsulfonyl, cyano, a group of the formula

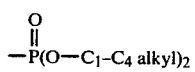

or a group of the formula —COOY$_1''$, wherein Y$_1''$ is as defined above, and R$_4^{Iv}$ is hydrogen or $C_1$-$C_4$alkyl.

In the compounds of the formula (1) to (5), R$_4$, R$_4'$, R$_4''$, R$_4'''$ and R$_4^{Iv}$ are preferably hydrogen.

Particularly preferred compounds are those of the formula

wherein R$_1^{Iv}$ is $C_1$-$C_4$alkylsulfonyl, cyano,

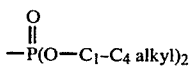

or —COOY$_1'''$, wherein Y$_1'''$ is $C_1$-$C_4$alkyl, $C_2$-$C_4$hydroxyalkyl, $C_3$-$C_6$alkoxyalkyl, —CH$_2$—CH$_2$—O)$_{n'}$(-$C_1$-$C_4$alkyl), wherein n' is an integer from 1 to 4, or is $C_3$-$C_6$carbalkoxyalkyl, $C_2$-$C_6$carboxyalkyl or $C_2$-$C_5$-cyanoalkyl; R$_2'''$ is hydrogen or halogen; and R$_3^v$ is $C_1$-$C_4$alkylsulfonyl, cyano,

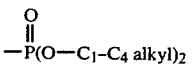

or —COOY$_1'''$, wherein Y$_1'''$ is as defined above.

In particularly preferred compounds of the formula (6), R$_1^{Iv}$ is cyano or —COOY$_1'''$, wherein Y$_1'''$ is $C_1$-$C_4$alkyl, $C_2$-$C_4$hydroxyalkyl, $C_3$-$C_6$alkoxyalkyl or —CH$_2$CH$_2$—O)$_{n'}$($C_1$-$C_4$alkyl), wherein n' is an integer from 1 to 4, R$_3^v$ is cyano or —COOY$_1'''$, wherein Y$_1'''$ is as defined above, and R$_2'''$ is hydrogen or chlorine.

In the most preferred compounds of the formula (6), R$_1^{Iv}$ is cyano, R$_2'''$ is hydrogen and R$_3^v$ is cyano or COOY$_1^{Iv}$, wherein Y$_1^{Iv}$ is $C_1$-$C_4$alkyl, $C_2$-$C_4$hydroxyalkyl, $C_3$-$C_6$alkoxyalkyl or (—CH$_2$—CH$_2$—O)$_{n'}$($C_1$-$C_4$alkyl), wherein n' is an integer from 1 to 4, with R$_3^v$ preferably being CN.

The 4styryl-4'-vinylbiphenyls of the formula (1) and, accordingly, also those of the sulformulae (2) to (6), can be obtained e.g. by a novel process which comprises reacting a biphenyl-4,4'-dialdehyde of the formula

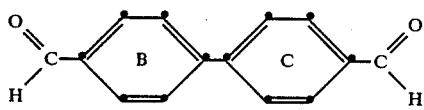

with a compound of the formula

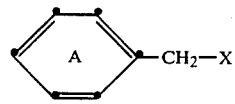

to give an aldehyde of the formula

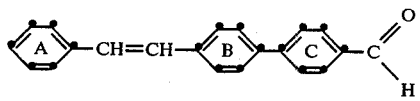

and then reacting this aldehyde further with a compound of the formula

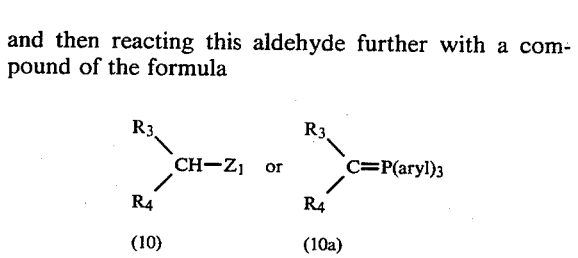

to give a compound of the formula (1), in which formulae above A, B, C, R$_3$ and R$_4$ are as defined for formula (1) and X and Z$_1$ are the same or different and each independently of the other is hydrogen or a radical of the formula —COOZ, wherein Z is hydrogen or alkyl,

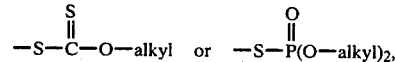

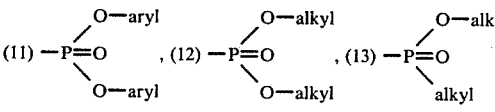

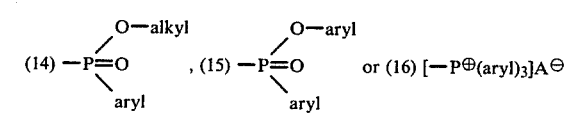

wherein A$^\ominus$ is a monovalent colourless anion, and, if desired, converting a compound of the formula (1) so obtained, by conventional methods, into another compound of the formula (1).

A colourless anion A$^\ominus$ can be any anion and has no influence on the operability of the process of the invention. Preferred anions A$^\ominus$ are halide ions, e.g. chloride or bromide, alkyl sulfate or aryl sulfonate ions, e.g. phenylsulfonate, tolylsulfonate and chlorophenylsulfonate ions. Other customary anions can also be used. The preferred meanings of aryl in formula (10a) and in formulae (11), (14), (15) and (16) are the same as those cited at the outset.

Compounds of the formula (1) obtained by the process of the invention can be converted by methods knosn per se into other compounds of the formula (1), for example by esterification, hydrolysis, transesterification, oxidation, reduction, halogenation, amidation etc. For example, a carboxylic acid ester group R$_1$, R$_2$ and-/or R$_3$ can be hydrolysed to the corresponding acid, this latter converted into the acid chloride, which in turn is reacted with an alcohol to another carboxylic acid ester group.

It is preferred to carry out the process described above by using compounds of the formula (8) and (10) in which each of X or $Z_1$ independently of the other is a group of the formula (11), (12), (13), (14) or (15), with a group of the formula (12) being preferred. Alkyl groups in the formulae (11) to (16) preferably contain 1 to 6, most preferably 1 to 4, carbon atoms. Suitable aryl radicals are, in particular, an unsubstituted phenyl radical or a phenyl radical which is substituted by chlorine or $C_1$–$C_4$alkyl.

Alternatively, the compounds of the formula (1) can also be obtained by reacting a biphenyl-4,4'-dialdehyde of the formula

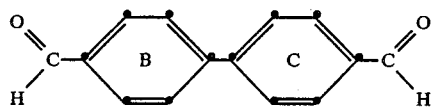 (7)

with a compound of the formula

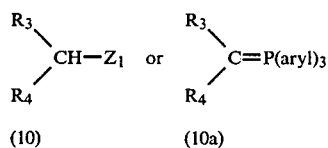

(10)      (10a)

to give an aldehyde of the formula

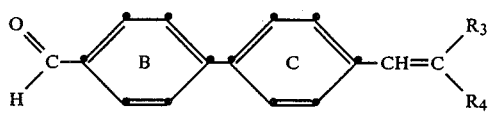 (17)

and then reacting this aldehyde further with a compound of the formula

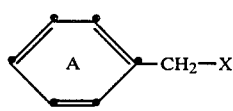 (8)

to a compound of the formula (1), in which formulae above A, B, C, $R_3$, $R_4$, X and $Z_1$ are as defined for formulae (1), (8) and (10).

In this process too, it is preferred to use those compounds of the formulae (8) and (10) in which each of X and $Z_1$ independently is one of the groups of the formulae (11) to (15), preferably a group of the formula (12).

The reaction of a compound of the formulae (7), preferably biphenyl-4,4'-dialdehyde itself, with a compound of the formula (8) or with a compound of the formula (10) or (10a) (first step), is preferably carried out in the presence of an alkaline condensing agent which acts as proton acceptor. Examples of such condensing agents are hydroxides, hydrides, alkoxides and amides of alkali metals or alkaline earth metals, monomeric or polymeric strongly basic amines, quaternary ammonium hydroxides and resin exchangers of the OH series. Especially preferred bases are sodium and potassium hydroxide, sodium methylate and sodium ethylate. A mixture of different bases can also be used. The amount of condensing agent employed varies within wide limits. It is advantageous to use the equivalent amount; but an excess can also be used. The second step into [reaction of the monoaldehyde of the formula (9) or (17) with a compound of the formula (10) or (10a) or of the formula (8)], is preferably carried out in the presence of the same condensing agents as indicated for the first step.

The process of the invention is conveniently carried out in a solvent which is inert under the reaction conditions. Suitable solvents of this kind are e.g. hexane, octane, cyclohexane, toluene, xylene, chlorobenzene etc.; formamide, dimethyl formamide, N-methylpyrrolidone, acetonitrile, dimethyl sulfoxide etc.; methanol, ethanol, isopropanol, hexanol etc. It is also possible to carry out the process of the invention in water or in mixtures containing water, in the presence or absence of phase transfer catalysts.

The first step is preferably carried out in a solvent in which the monoaldehydes of the formulae (9) and (17) are limitedly soluble, e.g. in methanol, ethanol, hexane or toluene. The aldehydes precipitate during the reaction together with small amounts of the corresponding symmetrical compounds and can be isolated by filtration or preferably further reacted without isolation. If the intermediates are isolated, then they are preferably further used without purification.

The reaction of the monoaldehydes of the formulae (9) and (17) with a compound of the formula (10) or (10a) or of the formula (8) [second step] is preferably conducted in a solvent in which the monoaldehydes are partially or completely soluble. Examples or suitable solvents of this kind are, in particular, aprotic dipolar solvents, e.g. dimethyl and diethyl formamide and dimethyl sulfoxide.

Depending on the chosen solvent, the reaction temperature varies within wide limits and can be readily ascertained by preliminary experiments. The first step is conveniently carried out in the temperature range from 0° to 50° C., with the preferred range being from 20° to 30° C. A suitable temperature range for the second step is from 20° to 100° C., preferably from 30° to 50° C.

The compounds of the formulae (8), (10) and (10a) used as starting materials are known or can be readily prepared by methods analogous to known ones. In this connection, attention is drawn to German Offenlegungsschrift No. 19 21 466, British patent specification Nos. 920 988 and 929 436, and German Offenlegungsschrift No. 26 02 750. The starting compounds of the formula (7), especially the unsubstituted biphenyl-4,4'-dialdehyde, are also known. Substituted compounds of the formula (7) can be obtained in similar manner to the unsubstituted dialdehyde.

The monoaldehydes of the formula (9) obtained as intermediates in the first mentioned process of the invention are novel and likewise constitute an object of the invention.

Particularly interesting novel compounds of the formula (9) are those of the formula

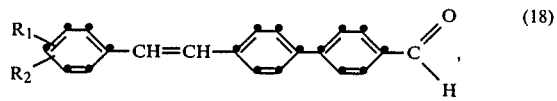 (18)

wherein each of $R_1$ and $R_2$ is hydrogen or a non-chromophoric substituent, or both together in the ortho-position complete a fused ring, and $R_1$ is preferably hydrogen, halogen, or alkyl, alkoxy or alkylsulfonyl, each unsubstituted or substituted by non-chromophoric groups; phenyl, phenylalkyl, phenylsulfonyl, phenoxy or phenylalkoxy, each unsubstituted or substituted by non-chromophoric groups; or is cyano or a group of the formula —COOY$_1$, —CONY$_1$Y$_2$ or —SO$_2$NY$_1$Y$_2$, wherein each of Y$_1$ and Y$_2$ independently is hydrogen, alkenyl, propargyl, cycloalkyl containing 5 or 6 ring carbon atoms, alkyl, phenyl or phenylalkyl, each unsubstituted or substituted by non-chromophoric groups; or Y$_1$ and Y$_2$, together with the nitrogen atom to which they are attached, are a 5- or 6-membered saturated heterocyclic ring which can additionally contain 1 or 2 hetero-atom as ring members and can also be substituted by alkyl groups; or wherein Y$_1$ in the group —COOY$_1$ can also additionally by a salt-forming cation; or R$_1$ is a group of the formula

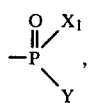

wherein each of X$_1$ and Y independently of the other is halogen, alkyl, alkenyl, phenyl, phenylalkyl, hydroxy, alkoxy, phenylalkoxy, cycloalkoxy, phenoxy, amino, mono- or dialkylamino, phenylalkylamino, acylamino, phenylamino, cycloalkylamino, morpholino, piperidino or pyrrolidino; or R$_1$ together with R$_2$ in the ortho-position are the radical of the formula —CH=CH—CH=CH—, —O—CH$_2$—O— or —O—CH$_2$—CH$_2$—O—; R$_2$ is hydrogen, halogen, or alkyl or alkoxy, each unsubstituted or substituted by non-chromophoric groups; or R$_2$ together with R$_1$ in the ortho-position are the radical of the formula —CH=CH—CH=CH—, —O—CH$_2$—O— or —O—CH$_2$—CH$_2$—O—.

Compounds meriting attention are also those of the formula

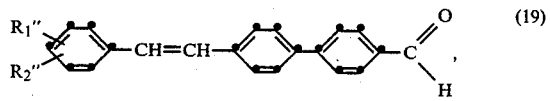 (19)

wherein R$_1$″ is hydrogen, halogen, C$_1$-C$_4$alkyl, C$_1$-C$_4$alkoxy, C$_1$-C$_4$alkylsulfonyl, cyano, or phenyl or phenylsulfonyl, each unsubstituted or substituted by chlorine, methyl and/or methoxy; or is a group of the formula —COOY$_1$′, —CONY$_1$′Y$_2$′ or —SO$_2$NY$_1$′Y$_2$′, wherein Y$_1$′ is hydrogen, C$_1$-C$_8$alkyl, C$_3$-C$_4$alkenyl, cyclohexyl, C$_2$-C$_4$hydroxyalkyl, C$_3$-C$_6$alkoxyalkyl, a radical of the formula —CH$_2$CH$_2$—O)$_n$(C$_1$-C$_4$alkyl), wherein n is an integer from 1 to 6, or is C$_6$-C$_9$phenoxyalkyl, C$_2$-C$_6$carboxyalkyl, C$_3$-C$_6$carbalkoxyalkyl, C$_2$-C$_5$cyanoalkyl, phenyl or benzyl, each unsubstituted or substituted by chlorine, methyl and/or methoxy, or is C$_3$-C$_7$dialkylaminoalkyl or phenethyl; Y$_2$′ is hydrogen, C$_1$-C$_4$alkyl, C$_3$-C$_4$alkenyl or C$_2$-C$_4$hydroxyalkyl; or Y$_1$′ and Y$_2$′, together with the nitrogen atom to which they are attached, are a 5- or 6-membered saturated heterocyclic ring which can additionally contain a further nitrogen or oxygen atom as ring member and which can be substituted by 1 or 2 C$_1$-C$_4$alkyl groups; or wherein Y$_1$′ in the group —COOY$_1$′ can additionally be an alkali metal ion or an ammonium ion; or R$_1$″ is a group of the formula

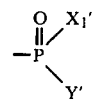

wherein each of X$_1$′ and Y′ independently of the other is C$_1$-C$_4$alkyl, benzyl, or phenyl which is unsubstituted or substituted by chlorine, methyl and/or methoxy; R$_2$″ is hydrogen, halogen or C$_1$-C$_4$alkyl; whilst R$_1$″ is preferably halogen, C$_1$-C$_4$alkylsulfonyl, cyano or a group of the formula —COOY$_1$‴, wherein Y$_1$″ is C$_1$-C$_8$alkyl, C$_3$-C$_4$alkenyl, C$_2$-C$_4$hydroxyalkyl, C$_3$-C$_6$alkoxyalkyl, a radical of the formula —CH$_2$CH$_2$—O)$_n$′(C$_1$-C$_4$alkyl), wherein n′ is an integer from 1 to 4, or is C$_2$-C$_6$carboxyalkyl, C$_3$-C$_6$carbalkoxyalkyl or C$_2$-C$_5$cyanoalkyl; or R$_1$″ is a group of the formula

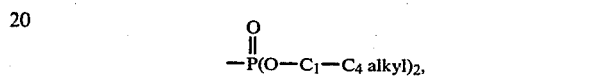

and R$_2$″ is preferably hydrogen or halogen.

Preferred intermediates are those of the formula

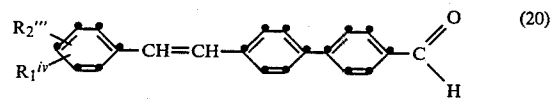 (20)

wherein R$_1^{iv}$ is C$_1$-C$_4$alkylsulfonyl, cyano,

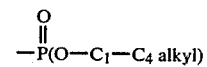

or —COOY$_1$‴, wherein Y$_1$‴ is C$_1$-C$_4$alkyl, C$_2$-C$_4$hydroxyalkyl, C$_3$-C$_6$alkoxyalkyl, (—CH$_2$—CH$_2$—O)$_n$′(-C$_1$-C$_4$alkyl), wherein n′ is an integer from 1 to 4, or is C$_3$-C$_6$carbalkoxyalkyl, C$_2$-C$_6$carboxyalkyl or C$_2$-C$_5$-cyanoalkyl, and R$_2$‴ is hydrogen or halogen; whilst R$_1^{iv}$ is preferably cyano or —COOY$_1$‴, wherein Y$_1$‴ is C$_1$-C$_4$alkyl, C$_2$-C$_4$hydroxyalkyl, C$_3$-C$_6$alkoxyalkyl or (—CH$_2$—CH$_2$—O)$_n$′(C$_1$-C$_4$alkyl), wherein n′ is an integer from 1 to 4, and R$_2$‴ is hydrogen or chlorine.

Particularly preferred compounds of the formula (20) are those in which R$_1^{iv}$ is cyano and R$_2$‴ is hydrogen.

The intermediates of the formula (9) are preferably obtained by reacting a biphenyl-4,4′-dialdehyde of the formula

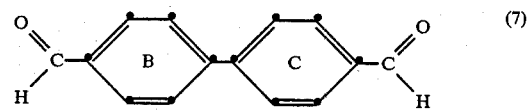 (7)

with a compound of the formula

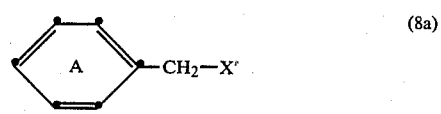 (8a)

in which formulae A, B and C are as defined for formula (1) and X′ is a radical of the formula

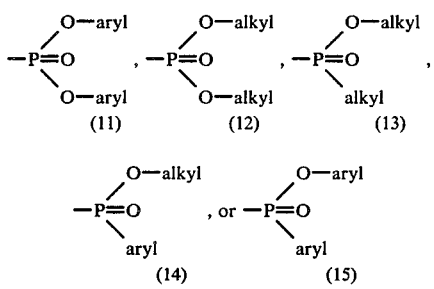

(11) (12) (13)

(14) (15)

This process corresponds to the first step of the first process for the production of 4-styryl-4'-vinylbiphenyls of the formula (1). The monoaldehyde of the formula (9), or of one of the subformulae (18) to (20), can be isolated from the reaction mixture and purified in conventional manner, e.g. if desired by repeated recrystallisation, with or without the addition of activated charcoal or fuller's earth. Purification can also be effected by column chromatography.

The same preferred reaction conditions (condensing agent, solvent, temperature etc.) can be chosen for the production of the intermediates of the formula (9) as have been previously described above for the first step of the process for the production of compounds of the formula (1).

The monoaldehydes of the formula (17) obtained as intermediates in the second variant of the process for the production of compounds of the formula (1) [reaction of a biphenyl-4,4'-dialdehyde of the formula (7) initially with a compound of the formula (8)], are also novel and therefore also constitute an object of the invention. Preferred monoaldehydes of the formula (17) have the formula

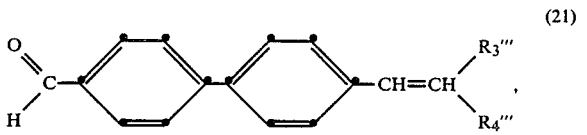

(21)

wherein $R_3'''$ and $R_4'''$ are as defined in formula (4). Preferably $R_3'''$ and $R_4'''$ have the meanings of $R_3^{1v}$ and $R_4^{1v}$ as defined for formula (5). Most preferably, in particularly preferred intermediates of the formula (21) $R_4'''$ is hydrogen and $R_3'''$ is cyano or $-COOY_1^{1v}$, wherein $Y_1^{1v}$ is $C_1-C_4$alkyl, $C_2-C_4$hydroxyalkyl, $C_3-C_6$alkoxyalkyl, $(-CH_2-CH_2-O)_n(C_1-C_4alkyl)$, wherein n' is an integer from 1 to 4, $C_3-C_6$carbalkoxyalkyl or $C_2-C_5$cyanoalkyl. The preferred identity of $R_3'''$, however, is cyano.

The invention also relates to a process for the production of the intermediates of the formula (17), which process preferably consists in reacting a compound of the formula (7) with a compound of the formula (10) or (10a), with the substituent $Z_1$ in formula (10) being one of the groups of the formulae (11) to (15).

This process corresponds to the first step of the second process for the production of 4-styryl-4'-vinylbiphenyls of the formula (1). The monoaldehyde of the formula (17) can be isolated from the reaction mixture is conventional manner and purified, e.g. if desired by repeated recrystallisation, with or without the addition of activated charcoal or fuller's earth. If desired, purification can also be effected by column chromatography.

The same preferred reaction conditions (condensing agent, solvent, temperature etc.) are chosen for the production of the intermediates of the formula (17) as have previously been described above for the first step of the process for the production of the compounds of formula (1).

The 4-styryl-4'-vinylbiphenyls of the formula (1) are used for whitening a very wide variety of synthetic, regenerated and natural organic materials of high molecular weight. This utility is also an object of the invention.

Without any restriction being implied by the following classification, the following groups of organic materials may be regarded as exemplifying material which can be treated with fluorescent whitening agents:

I. Synthetic organic material of high molecular weight:

(a). polymerisation products based on organic compounds containing at least one polymerisable carbon-carbon double bond, that is to say their homopolymers or copolymers as well as their aftertreatment products, for example, cross-linking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylates, acrylic acid, acrylonitrile, acrylamides and their methacrylic analogues, on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (for example ethylene glycol, terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;

(d) polyadducts such as polyurethanes (crosslinked and uncrosslinked) and epoxy resins.

II. Regenerated organic material, for example cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic material of animal vegetable origin, for example based on cellulose or proteins, such as cotton, wool, linen, silk, natural film-forming resins, starch and casein.

The organic material to be whitened and/or brightened can be in the most diverse states of processing (raw materials, semi-finished goods or finished goods). On the other hand, it can be in the form of a very wide variety of shaped structures, for example predominantly three-dimensional structures such as sheets, profiles, injection mouldings, various machined articles, chips, granules or foams; and also predominantly two-dimensional structures such as films, sheets, lacquers, coatings and impregnations; or predominantly one dimensional bodies such as filaments, fibres, flocks and wires. The above materials can, on the other hand, also be in an unshaped state, in the most diverse homogeneous or inhomogeneous forms of division, as for example in the form of powders, solutions, emulsions, dispersions, latices, pastes or waxes.

Fibrous material can be, for example, in the form of endless filaments (stretched or unstretched), staple fibres, flocks, hanks, textile filament yarns, threads, nonwovens, felts, waddings, flocked structures or woven textile or bonded textile fabrics, knitted fabrics, and papers, cardboards or paper pulps.

The compounds of the formula (1) to be used in the practice of this invention are of importance in particular for treating organic textile fabrics, especially woven textile fabrics. If it is desired to whiten fibres which can be in the form of staple fibres or endless filaments or in the form of hanks, woven fabrics, fleeces, flocked substrates or bonded fabrics, this is advantageously effected in an aqueous medium in which the compounds of the invention are finely dispersed (suspensions, so-called microdispersions or, where appropriate, solutions). If desired, dispersing agents, stabilisers, wetting agents and further assistants can be added during the treatment.

Application can be made from a neutral, alkaline or acid bath. The treatment is usually carried out in the temperature range from about 20° to 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermofixation application, or exhaust dyeing methods in dyeing machines).

The fluorescent whitening agents of the present invention can further be added to, or incorporated in, the materials before or during their processing to shaped articles. They can thus be added to the moulding or injection moulding compounds in the manufacture of films, sheets (e.g. rolling into polyvinyl chloride at elevated temperature) or moulded articles.

If synthetic or regenerated organic materials are formed by spinning processes or from spinning solutions/melts, the fluorescent whitening agents can be applied by the following methods:
addition to the starting materials (for example monomers) or intermediates (for example precondensates or prepolymers), that is to say before or during the polymerisation, polycondensation or polyaddition,
sprinkling in powder form on polymer chips or granules for spinning solutions/melts,
bath dyeing of polymer chips or granules for spinning solutions/melts,
metered addition to spinning melts or spinning solutions, and
application to the spun tow before stretching.

The fluorescent whitening agents of the present invention can also be employed e.g. in the following formulations:
(a) in mixtures with dyes (shading) or pigments (coloured pigments or especially, for example, white pigments), or as an additive to dyebaths, printing pastes, discharge pastes or reserve pastes, or for the aftertreatment of dyeings, prints or discharge prints;
(b) in mixtures with carriers, wetting agents, plasticisers, swelling agents, antioxidants, ultraviolet absorbers, heat stabilisers and chemical bleaching agents (chlorite bleach or bleaching bath additives),
(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft finishes, anti-soiling finishes, antistatic finishes, or antimicrobial finishes;
(d) incorporation of the fluorescent whitening agent in polymer carriers (polymerisation, polycondensation or polyaddition products, in dissolved or dispersed form, for use e.g. in coating agents, impregnating agents of binders (solutions, dispersions and emulsions) for textiles, nonwovens, paper and leather;
(e) as additives to a wide variety of industrial products in order to render these more marketable (for example improving the appearance of soaps, detergents, pigments);
(f) in spinning bath preparations, that is to say as additives to spinning baths which are used for improving the slip for the further processing of synthetic fibres, or from a special bath before the stretching of the fibre;
(g) in compositions for whitening organic materials of high molecular weight of the above kind, which compositions may contain conventional formulation additives and/or further fluorescent whitening agents belonging or other classes of whitener compounds;
(h) in combination with other substances which act as fluorescent whitening agents, and also as additives to master batches,
(i) as scintillators for various purposes of a photographic nature, for example for electrophotographic reproduction or supersensitising;
(j) depending on the substitution, as laser dyes.

The invention also relates to compositions which contain the fluorescent whitening agents of this invention.

Suitable formulation additives which such compositions may contain are e.g. assistants and extenders of widely different kinds, e.g. anhydrous sodium sulfate, sodium sulfate decahydrate, sodium chloride, sodium carbonate, alkali metal phosphates such as sodium or potassium orthophosphate, sodium or potassium pyrophosphate and sodium or potassium tripolyphosphates, or alkali metal silicates. The compositions of the invention also comprise aqueous formulations, e.g. also the application solutions with which textile fibres can be whitened and which contain conventional additives.

Particularly preferred compositions within the scope of the present invention are those which, in addition to containing a fluorescent whitening agent of one of the formulae (1) to (6) which gives a reddish hue on the substrate to be treated, also contain a fluorescent whitening agent which gives a greenish to bluish hue on the substrate. Such combinations have the advantage that a particularly pleasing neutral white effect of great brilliance can be obtained on textile fibres, especially on polyester fibres.

Accordingly, very advantageous compositions are those which contain one or more fluorescent whitening agents of the formulae (1) to (6) and, in addition, one or more fluorescent whitening agents of the class of the bis-styrylbenzenes, benzoxazolylstilbenes, 4,4'-divinylstilbenes, naphthalimides, 4,4'-bis-styrylbiphenyls, 4,4'-bis-triazolylstilbenes, bis-benzoxalolylthiophenes, naphthotriazol-2-yl-stilbenes (known from German Offenlegungsschrift specifications Nos. 25 39 537 and 25 39 461), or of the coumarins, e.g. pyrazolyl- and triazolylcoumarins (known from Swiss patent specifications Nos. 566 359 and 592 189), especially those which contain, as active ingredient, 10 to 99%, preferably 30 to 70%, of a fluorescent whitening agent of one of the formulae (1) to (6), and 90 to 1%, preferably 70 to 30%, of a fluorescent whitening agent of one of the above mentioned classes. Such combinations of fluorescent whitening agents need not contain further additives, i.e. they can be in the form of pure mixtures.

Particularly preferred substrates to be treated with the fluorescent whitening agents of this invention are those made of polyester, especially polyester textile materials.

If the whitening process is combined with a textile treatment or with finishing methods, the combined treatment can usually advantageously be carried out using appropriate stable preparations which contain the fluorescent whithener compounds in a concentration such that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. For example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., in which case it is generally advisable additionally to dry the fibrous material beforehand at moderately elevated temperature, for example in the range from at least 60° C. to about 130° C. The heat treatment in the dry state is then advantageously carried out at in the temperature range from 120° to 225° C., for example by heating in a drying chamber, by ironing within the specified temperature range or by treatment with dry, superheated steam. The drying and dry heat treatment can also be carried out in immediate succession or be combined in a single procedure.

The amount of fluorescent whitening agent of the present invention to be used, based on the weight of the material to be whitened, can vary within wide limits. A marked and lasting effect can be obtained even with very insignificant amounts, in certain cases 0.001 percent by weight. But it is also possible to use amounts of up to 0.8 percent by weight and, on occasion, up to 2 percent by weight. For most practical purposes, it is preferred to use amounts between 0.01 and 0.5 percent by weight.

Particularly preferred fields of use for the compounds of the invention are: whitening polyester, viz. both polyester fibres and fabrics by the exhaust or pad-heat process, and polyester spinning solutions/melts. Blends of polyester and cotton or wool are also very advantageously whitened with the compounds of the invention. Examples of further substrates which can advantageously by whitened with the compounds of formula (1) are: polyamide fibres, cellulose acetate fabric and polystyrene and polyvinyl chloride compositions. The most preferred utility, however, is the whitening of polyester fibres by the exhaust or pad-heat process.

The following Examples illustrate further the production and use of the compounds of the invention. In these Examples, as also throughout the rest of the specification, parts and percentages are by weight, unless otherwise stated. Melting and boiling points are uncorrected, unless otherwise indicated.

EXAMPLE 1

(a) 21 g of biphenyl-4,4'-dialdehyde are suspended in 200 ml of anhydrous methanol. With stirring and under nitrogen, 36 g of a 30% methanolic solution of sodium methylate are added to this suspension at 20°–25° C. over 15 minutes, whereupon an almost clear solution is obtained. With stirring and under nitrogen, a solution of 25.3 g of the phosphonate of the formula

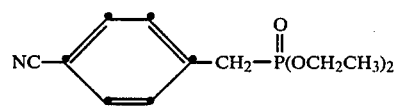

in 50 ml of anhydrous methanol is added at 20°–25° C. over 10 minutes and the reaction product precipitates in crystalline form immediately. The dense crystalline slurry is further stirred for 20 hours under nitrogen at 20°–25° C. and then filtered. The filter cake is washed with about 50 ml of anhydrous methanol and vacuum dried at 80° C. to constant weight, affording 29 g (about 93.7% of theory) of the aldehyde of the formula

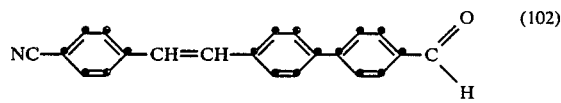

in the form of a yellow crystalline powder with a melting point of 192°–196° C.

Two recrystallisations from chlorobenzene give 19 g of the compound of the formula (102) in the form of yellow needles with a melting point of 197°–200° C.

The starting phosphonate of the formula (101) is prepared in accordance with Example 1 of German Offenlegungsschrift No. 1 921 466.

(b) 15.5 g of the 4-(4-cyanostyryl)-biphenyl-4'-aldehyde of the formula (102) and 11.2 g of triethyl phosphonoacetate of the formula

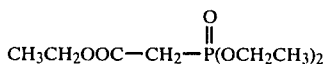

are suspended in 120 ml of dimethyl formamide. With stirring and under nitrogen, 18 g of a 30% methanolic solution of sodium methylate are added to this suspension at 30° C. over 30 minutes and the temperature rises to 40° C. Initially an almost clear solution is obtained, from which the reaction product precipitates as a dense crystalline slurry towards the end of the addition of sodium methylate. The reaction mixture is then further stirred for 4 hours at 30° C. under nitrogen, then neutralized at 0° C. with 12 ml of glacial acetic acid and diluted with 200 ml of water. The reaction product is filtered with suction, washed neutral with water and vacuum dried at 80° C. to constant weight, affording 18 g (c. 98.5% of theory) of the compound of the formula

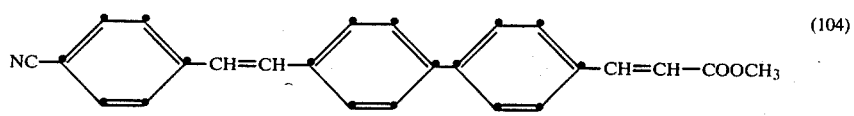
(104)

in the form of a pale yellow crystalline powder with a melting point of 221°–226° C.

Two recrystallisations from chlorobenzene using activated charcoal give 14 g of the compound of the formula (104) in the form of pale yellow needles with a melting point of 230°–232° C.

EXAMPLE 2

The procedure described in Example (1b) is repeated, except that an ethanolic solution of sodium ethylate (obtained by dissolving 2.3 g of sodium in 50 ml of anhydrous ethanol) is used instead of the methanolic solution of sodium methylate. Yield: 18.2 g (c. 95.9% of theory) of the compound of the formula

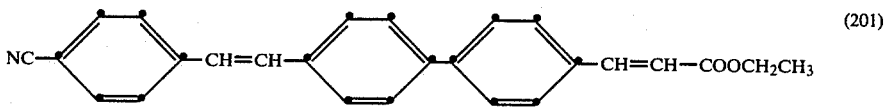
(201)

in the form of a yellow crystalline powder with a melting point of 209°–215° C.

Three recrystallisations from chlorobenzene using activated charcoal give 10 g of the compound of the formula (201) in the form of pale yellow needles with a melting point of 219°–222° C.

EXAMPLE 3

With stirring, 61.9 g of the 4-(4-cyanostyryl)-biphenyl-4'-aldehyde of the formula (102) and 30 g of anhydrous malonic acid are refluxed in 200 ml of dry pyridine and 0.5 ml of piperidine for 20 hours. The reaction mixture is then cooled to room temperature and diluted by stirring in 500 ml of water. The precipitate is filtered with suction and the filter cake is washed with dilute hydrochloric acid, water and methanol, and vacuum dried to constant weight at 80° C. Yield: 70.1 g (c. 100% of theory) of the compound of the formula

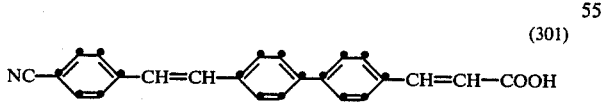
(301)

in the form of a pale yellow crystalline powder with a melting point of above 300° C.

One recrystallisation from dimethyl formamide yields 36.2 g of the compound of the formula (301) in the form of pale yellow needles with a melting point of above 300° C.

EXAMPLE 4

With stirring, 18.1 g of the acid of the formula (301) are refluxed for 2 hours in 200 ml of chlorobenzene, 50 ml of thionyl chloride and 0.5 ml of dimethyl formamide. After dilution with 150 ml of chlorobenzene, 200 ml of the reaction mixture are distilled off. Then 50 ml of n-propanol are added dropwise at reflux temperature to the obtained solution of the acid chloride of the formula

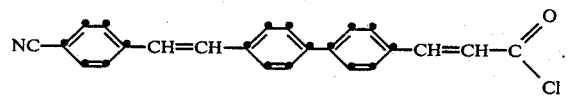
(401)

The reaction mixture is kept at reflux temperature for 16 hours, then decolourised with activated charcoal and concentrated to a volume of about 70 ml. The reaction product precipitates at low temperature and is filtered with suction and vacuum dried at 80° C. Yield: 11.4 g (c. 57.9% of theory) of the compound of the formula

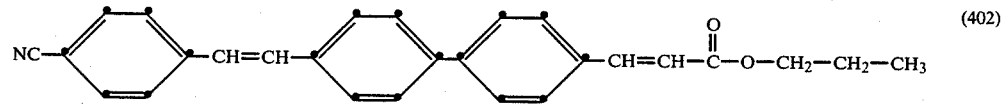
(402)

in the form of a yellow crystalline powder with a melting point of 157°–160° C.

Two recrystallisations from toluene using activated charcoal give 7.1 g of the compound of the formula (402) in the form of pale yellow needles with a melting point of 159°–161° C.

EXAMPLE 5

The procedure of Example 4 is repeated, using isopropanol instead of n-propanol, to give 15.3 g (c. 77.8% of theory) of the compound of the formula

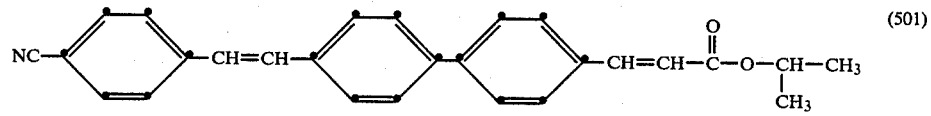
(501)

in the form of a pale yellow crystalline powder with a melting point of 201°–206° C.

Two recrystallisations from toluene using activated charcoal give 5.6 g of the compound of the formula (501) in the form of pale yellow crystals with a melting point of 209°-210° C.

EXAMPLE 6

18.3 g of the methyl ester of the formula (104) (see Example 1b), 60 g of ethylene glycol monomethyl ether and 250 ml of dichlorobenzene are heated, with stirring, to 120° C. and then 1 ml of tetrabutyl orthotitanate monomer is added at this temperature to give a clear solution. The reaction mixture is further stirred for 2 hours at 130° C. and then concentrated to a volume of about 70 ml. The reaction product precipitates at low temperature and is filtered with suction and vacuum dried at 80° C., affording 15.5 g (c. 75.7% of theory) of the compound of the formula

in the form of a pale yellow crystalline powder with a melting point of 145°-149° C.

Two recrystallisations from chlorobenzene using activated charcoal give 10 g of the compound of the formula (601) in the form of pale yellow needles with a melting point of 149°-151° C.

The compounds listed in Table I of the general formula

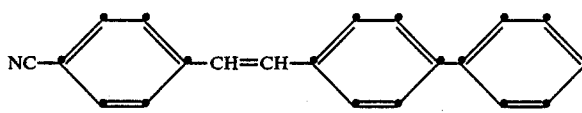

are prepared in similar manner, starting from the compound of the formula (104), by reaction with the corresponding alcohol.

TABLE I

| Compound No. | R | Melting point (°C.) |
|---|---|---|
| 602 | —CH$_2$—CH$_2$—O—CH$_2$—CH$_3$ | 138–139 |
| 603 | —CH—CH$_2$—O—CH$_3$<br>\|<br>CH$_3$ | 149–151 |
| 604 | —CH$_2$—CH$_2$—CH—CH$_3$<br>\|<br>O—CH$_3$ | 139–141 |
| 605 | —CH$_2$—CH$_2$—O—CH$_2$—CH$_2$—O—CH$_3$ | 117–120 |

EXAMPLE 7

12.3 g of the 4-(4-cyanostyryl)-biphenyl-4'-aldehyde of the formula (102) and 7 g of diethyl cyanomethylphosphonate of the formula

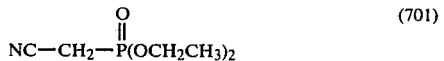

are reacted in 120 ml of dimethyl formamide as described in Example (1b). Yield: 12.5 g (c. 94.6% of theory) of the compound of the formula

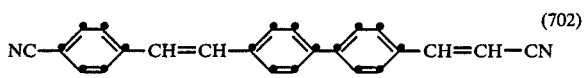

in the form of a yellow crystalline powder with a melting point of 195°-202° C.

Three recrystallisations from chlorobenzene using activated charcoal give 6.5 g of the compound of the formula (702) in the form of pale yellow crystals with a melting point of 203°-206° C.

EXAMPLE 8

(a) 63 g of biphenyl-4,4'-dialdehyde are suspended in 500 ml of anhydrous methanol. With stirring and under nitrogen, 108 g of a 30% methanolic solution of sodium methylate are added to this suspension at 20°-25° C. over 15 minutes, whereupon an almost clear solution is obtained. With stirring and under nitrogen, 76 g of the phosphonate of the formula

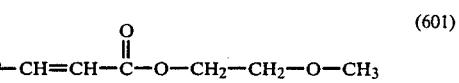

are added at 20°-25° C. over 30 minutes and the reaction product slowly precipitates in crystalline form. The crystalline suspension is further stirred for 20 hours under nitrogen at 20°-25° C. and then filtered. The filter cake is washed with about 70 ml of anhydrous methanol and vacuum dried at 80° C. to constant weight, affording 65.5 g (c. 70.6% of theory) of the aldehyde of the formula

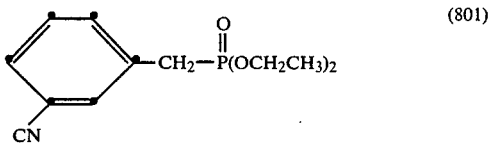

in the form of a yellow crystalline powder with a melting point of 137°-144° C.

Two recrystallisations from chlorobenzene give 31.5 g of the aldehyde of the formula (802) in the form of yellow needles with a melting point of 165°-167° C.

The starting phosphonate of the formula (801) is prepared in accordance with Example 2 of British Pat. No. 920 988.

(b) 15.5 g of the 4-(3-cyanostyryl)-biphenyl-4'-aldehyde of the formula (802) and 8.9 g of diethyl cyanomethylphosphonate of the formula (701) in 100 ml of dimethyl formamide are reacted as described in Example (1b), affording 15.6 g (c. 93.8% of theory) of the compound of the formula

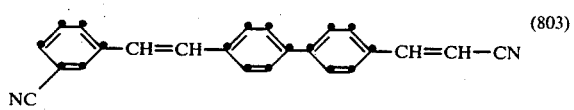
(803)

in the form of a pale yellow crystalline powder with a melting point of 204°–210° C.

Three recrystallisations from chlorobenzene using activated charcoal give 11 g of the compound of the formula (803) in the form of pale yellow crystals with a melting point of 210°–212° C.

EXAMPLE 9

(a) 84 g of biphenyl-4,4'-dialdehyde are suspended in 920 ml of anhydrous ethanol and the suspension is heated to reflux temperature and then cooled to room temperature. With stirring and under nitrogen, 144 g of a 30% methanolic solution of sodium methylate are added at room temperature over 15 minutes to the suspension. With stirring and under nitrogen, a solution of 101.2 g of the phosphonate of the formula

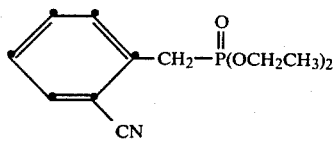
(901)

in 80 ml of anhydrous ethanol are added at room temperature over 15 minutes to the resultant almost clear solution, whereupon the reaction product slowly precipitates in crystalline form. The crystalline suspension is then further stirred for 20 hours at room temperature under nitrogen. The crystals are then collected by filtration, washed with about 100 ml of anhydrous ethanol and vacuum dried at 80° C. to constant weight. Yield: 80.5 g (c. 65.1% of theory) of the aldehyde of the formula

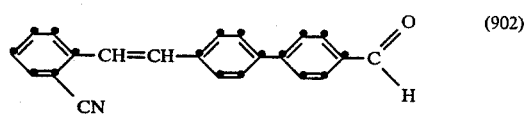
(902)

in the form of a pale yellow crystalline powder with a melting point of 161°–168° C.

Two recrystallisations from chlorobenzene using activated charcoal give 61 g of the compound of the formula (902) in the form of pale yellow needles with a melting point of 169°–171° C.

The starting phosphonate of the formula (901) is prepared in analogy to Example 1 of German Offenlegungsschrift 1 921 466 and purified by distillation (b.p.$_{0.35}$: 136°–138° C.).

(b) 15.5 g of the 4-(2-cyanostyryl)-biphenyl-4'-aldehyde of the formula (902) and 11.2 g of triethyl cyanomethylphosphonate of the formula (103) are reacted in 100 ml of dimethyl formamide as described in Example (1b), affording 17.5 g (c. 95.7% of theory) of the compound of the formula

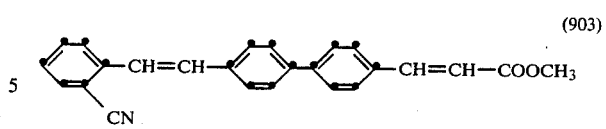
(903)

in the form of a pale yellow powder with a melting point of 154°–161° C.

Two recrystallisations from chlorobenzene using activated charcoal give 10 g of the compound of the formula (903) in the form of pale yellow needles with a melting point of 167°–169° C.

EXAMPLE 10

The procedure described in Example (9b) is repeated, except that an ethanolic solution of sodium ethylate (obtained by dissolving 2.3 g of sodium in 50 ml of anhydrous ethanol) is used instead of the methanolic solution of sodium methylate. Yield: 17.9 g (c. 94.3% of theory) of the compound of the formula

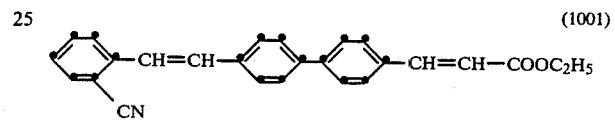
(1001)

in the form of a yellow crystalline powder with a melting point of 144°–152° C.

Two recrystallisations from chlorobenzene using activated charcoal give 7.2 g of the compound of the formula (1001) in the form of pale yellow needles with a melting point of 175°–180° C.

EXAMPLE 11

15.5 g of the 4-(2-cyanostyryl)-biphenyl-4'-aldehyde of the formula (902) and 8.9 g of diethyl cyanomethylphosphonate of the formula (701) are reacted in 100 ml of dimethyl formamide as described in Example (1b), affording 16.1 g (c. 96.8% of theory) of the compound of the formula

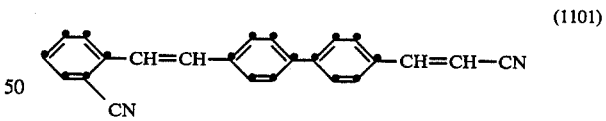
(1101)

in the form of a pale yellow powder with a melting point of 185°–202° C.

Three recrystallisations from chlorobenzene using activated charcoal give 7.5 g of the compound of the formula (1101) in the form of pale yellow needles with a melting point of 207°–211° C.

EXAMPLE 12

(a) 42 g of biphenyl-4,4'-dialdehyde are suspended in 400 ml of anhydrous methanol. With stirring and under nitrogen, 72 g of a 30% methanolic solution of sodium methylate are added to this suspension at 20°–25° C. over 15 minutes, whereupon an almost clear solution is obtained. With stirring and under nitrogen, a solution of 52 g of the phosphonate of the formula

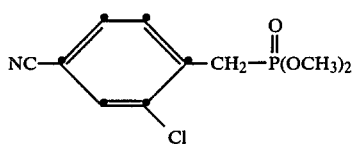
(1201)

in 100 ml of anhydrous methanol is added at 20°–25° C. over 15 minutes and the reaction product precipitates in crystalline form immediately. The dense crystalline slurry is further stirred for 26 hours under nitrogen at 20°–25° C. and then filtered. The filter cake is washed with about 100 ml of anhydrous methanol and vacuum dried at 80° C. to constant weight, affording 62.5 g (c. 90.9% of theory) of the aldehyde of the formula

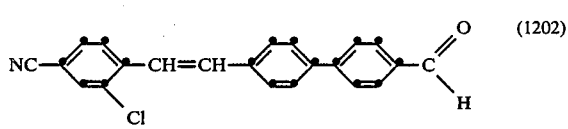
(1202)

in the form of a yellow crystalline powder with a melting point of 139°–164° C.

Two recrystallisations from chlorobenzene give 30.2 g of the compound of the formula (1202) in the form of yellow needles with a melting point of 152°–154° C.

(b) 17 g of the 4-(2-chloro-4-cyanostyryl)-biphenyl-4′-aldehyde of the formula (1202) and 9 g of diethyl cyanomethylphosphonate of the formula (701) are reacted in 100 ml of dimethyl formamide as described in Example (1b), affording 17 g (c. 92.9% of theory) of the compound of the formula

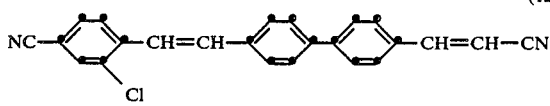
(1205)

in the form of a yellow crystalline powder with a melting point of 150°–158° C.

Two recrystallisations from dimethyl formamide using activated charcoal give 5 g of the compound of the formula (1205) in the form of pale yellow needles with a melting point of 186°–189° C.

The starting phosphonate of the formula (1201) is prepared as follows:

360 g of 3-chloro-4-methylaniline are diazotised as described by A. Goldberg and W. Kelly, J. Chem. Soc. 1947, 637–641. The aqueous solution of the diazonium salt is added at boiling temperature to a solution prepared from sodium cyanide and nickel(II)chloride in water. Yield: 216.4 g (c. 57.1% of theory) of the nitrile of the formula

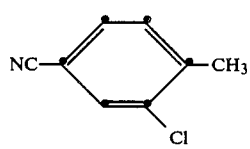
(1203)

in the form of a white crystalline powder with a melting point of 47°–49° C.

151.6 g of the nitrile of the formula (1203) are taken up in 700 ml of carbon tetrachloride and to this solution are added 187 g of N-bromosuccinimide and 2 g of dibenzoyl peroxide. The suspension obtained is heated for 24 hours to reflux temperature, then cooled to room temperature and filtered with suction. The filter cake is washed with 150 ml of carbon tetrachloride and the filtrate is vacuum concentrated to dryness, affording 230.8 g of a yellow oil. One recrystallisation from ethanol gives 125.8 g (c. 54.6% of theory) of the compound of the formula

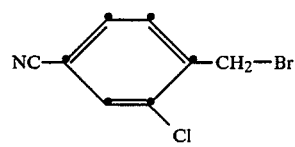
(1204)

in the form of a white crystalline powder with a melting point of 83°–85° C.

With stirring, 208 g of fused bromide of the formula (1204) are added dropwise at 100°–105° C. over 1 hour to 350 ml of trimethyl phosphite. During this addition methylene chloride escapes from the reaction mixture. The reaction mixture is then initially stirred for 1 hour at 110°–115° C. and then for 2 hours at 120°–125° C., during which time a portion of the excess trimethyl phosphite is distilled off. Excess trimethyl phosphite still remaining is then removed from the reaction mixture in vacuo, affording 220 g (c. 93.9% of theory) of the compound of the formula (1201) in the form of a brownish crystalline mass with a melting point of 85°–87° C. This crude phosphonate is purified by distillation, to give 197 g of pure phosphonate of the formula (1201) in the form of white crystals with a melting point of 89°–90° C. (b.p.$_{0.04}$: 150°–152° C.).

EXAMPLE 13

(a) 42 g of biphenyl-4,4′-dialdehyde are reacted with 52 g of the phosphonate of the formula

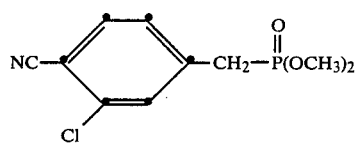
(1301)

as described in Example (12a), giving 55.2 g (c. 80.3% of theory) of the aldehyde of the formula

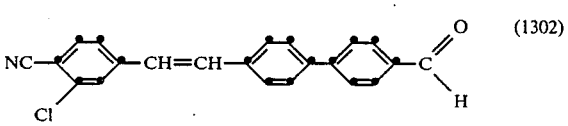
(1302)

in the form of a yellow crystalline powder with a melting point of 184°–205° C.

Two recrystallisations from chlorobenzene using activated charcoal give 35.5 g of the compound of the formula (1302) in the form of yellow needles with a melting point of 198°–200° C.

(b) 17 g of the 4-(3-chloro-4-cyanostyryl)-biphenyl-4′-aldehyde of the formula (1302) and 9 g of dimethyl cyanomethylphosphonate of the formula (701) are reacted in 100 ml of dimethyl formamide as described in Example (1b). Yield: 17.2 g (c. 93.8% of theory) of the compound of formula

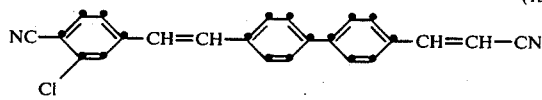
(1305)

in the form of a yellow crystalline powder with a melting point of 219°–225° C.

Two recrystallisations from chlorobenzene using activated charcoal give 11 g of the compound of the formula (1305) in the form of pale yellow crystals with a melting point of 226°–227° C.

The starting phosphonate of the formula (1301) is prepared as follows:

204 g of 2-chloro-4-methylaniline are diazotised by the method of A. Goldberg and W. Kelly, J. Chem. Soc. 1947, 637–641, and the aqueous solution of the diazonium salt is reacted with sodium cyanide as described in Example 12, giving 88.9 g (c. 40.7% of theory) of the nitrile of the formula

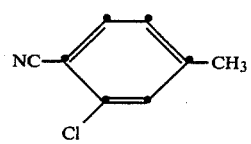
(1303)

in the form of a white crystalline powder with a melting point of 60°–61° C.

88 g of this nitrile are reacted with 109 g of N-bromosuccinimide as described in Example 12, giving 140 g of a yellow oil which, after one recrystallisation from ethanol, yields 93 g (c. 69.6% of theory) of the compound of the formula

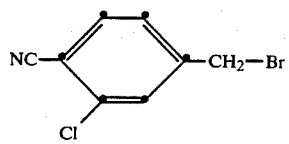
(1304)

in the form of a white crystalline powder with a melting point of 41°–44° C.

93 g of the bromide of the formula (1304) are reacted with 120 ml of trimethyl phosphite as described in Example 12, giving 102 g (c. 97.4% of theory) of a brownish oil. This crude phosphonate is purified by distillation, affording 70.5 g of pure phosphonate of the formula (1301) in the form of white crystals with a melting point of 71°–73° C. (b.p.$_{0.05}$: 148°–150° C.).

EXAMPLE 14

(a) 42 g of biphenyl-4,4'-dialdehyde are suspended in 200 ml of anhydrous ethanol. With stirring and under nitrogen, 160 ml of a 2.5 molar solution of sodium ethylate are added to this suspension at 20°–25° C. over 15 minutes, whereupon an almost clear solution is obtained. With stirring and under nitrogen, 60 g of the phosphonate of the formula

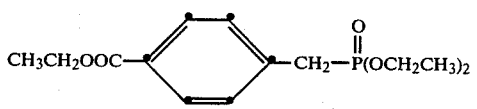
(1401)

are added at 20°–25° C. over 15 minutes and the reaction product precipitates in crystalline form immediately. The dense crystalline slurry is then stirred for 6 hours under nitrogen at 20°–25° C., diluted with 200 ml of ethanol, and then filtered. The filter cake is washed with about 100 ml of ethanol and vacuum dried at 80° C. to constant weight, affording 62 g (c. 87% of theory) of the aldehyde of the formula

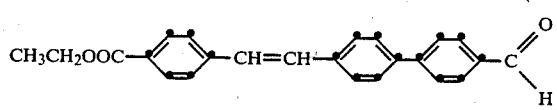
(1402)

in the form of a yellow crystalline powder with a melting point of 176°–180° C.

Two recrystallisations from chlorobenzene using activated charcoal give 44.5 g of the compound of the formula (1402) in the form of yellow needles with a melting point of 180°–183° C.

The starting phosphonate of the formula (1401) is prepared in accordance with Example 2 of British Pat. No. 929 436 and purified by distillation (b.p.$_{0.25}$: 181°–185° C.).

(b) 17.8 g of the 4-(4-carboethoxystyryl)-biphenyl-4'-aldehyde of the formula (1402) and 9 g of diethyl cyanomethylphosphonate of the formula (701) are reacted in 120 ml of dimethyl formamide as described in Example (1b), using 22 ml of a 2.5 molar solution of sodium ethylate instead of 18 g of a 30% methanolic solution of sodium methylate. Yield: 17.5 g (c. 93% of theory) of the compound of the formula

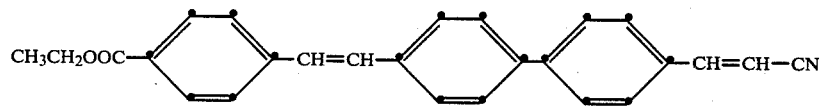
(1403)

in the form of a yellow crystalline powder with a melting point of 194°–200° C.

Two recrystallisations from chlorobenzene using activated charcoal give 11.5 g of the compound of the formula (1403) with a melting point of 199°–201° C.

The compound of the formula

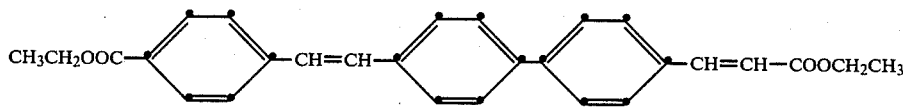
(1404)

EXAMPLE 15

17.8 g of the 4-(4-carboethoxystyryl)-biphenyl-4'-aldehyde of the formula (1402) and 9 g of diethyl cyanomethylphosphonate of the formula (701) are reacted in 120 ml of dimethyl formamide in the presence of 10 g of a 30% methanolic solution of sodium methylate as described in Example (1b). Yield: 17.5 g (c. 96% of theory) of the compound of the formula

(1501)

in the form of a yellow crystalline powder with a melting point of 216°–225° C.

Two recrystallisations from chlorobenzene using activated charcoal give 13 g of the compound of the formula (1501) in the form of pale yellow crystals with a melting point of 226°–228° C.

The compounds of the formula

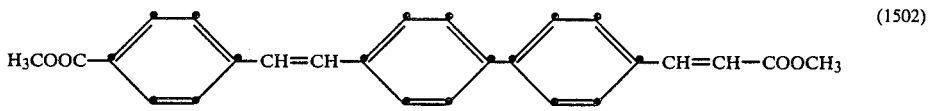
(1502)

is obtained in similar manner.

EXAMPLE 16

15.2 g of the compound of the formula (1403) are dissolved in 250 ml of 1,2-dichlorobenzene. To the clear solution are added 50 ml of 2-methoxyethanol and 1 ml of tetrabutyl orthotitanate. The reaction mixture is stirred for 2 hours at 130° C., then concentrated to a volume of 150 ml and left to crystallise out, with stirring. The reaction product is filtered with suction, washed with chlorobenzene and vacuum dried to constant weight at 100° C. Yield: 15 g (c. 94% of theory) of the compound of the formula

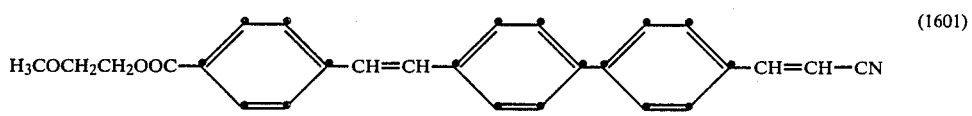
(1601)

in the form of a yellow crystalline powder with a melting point of 164°–170° C.

Two recrystallisations from chlorobenzene using activated charcoal give 10.5 g of the compound of the formula (1601) in the form of pale yellow crystals with a melting point of 168°–170° C.

The compounds of the following formulae are prepared in similar manner by reacting the compound of the formula (1403) with a corresponding alcohol (transesterification):

(1602)

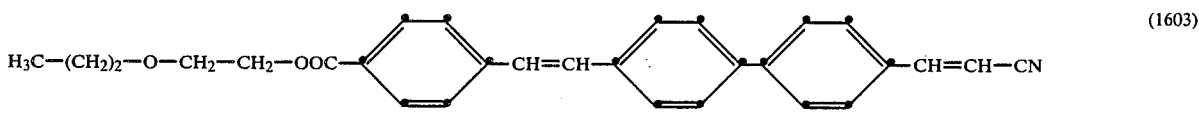
(1603)

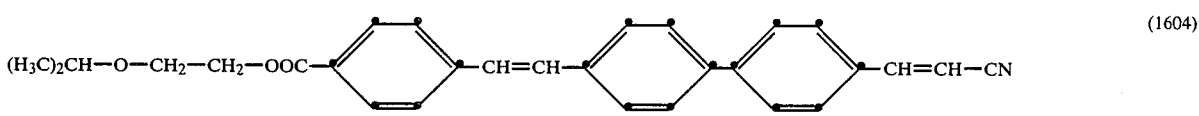
(1604)

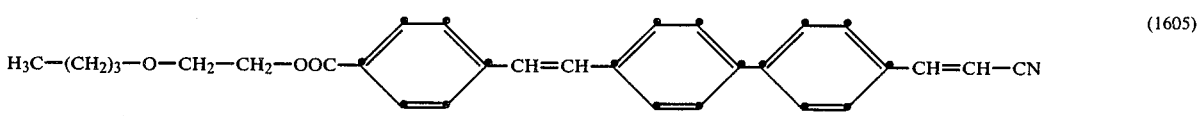
(1605)

(1606)

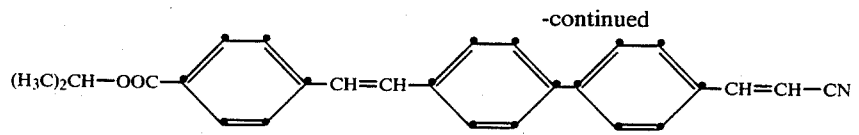

(1607)

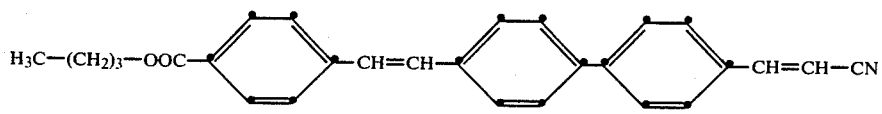

(1608)

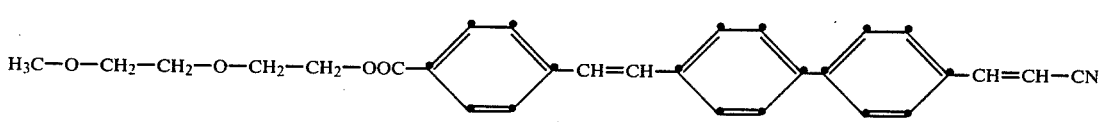

(1609)

(1610)

EXAMPLE 17

1 g of the compound of the formula (702) is dispersed in 1 liter of water. 7.5 ml of this dispersion are added to 300 ml of water which contain 0.1 of a fatty alcohol polyglycol ether. This dispersion is heated to 60° C. and then a polyester fabric weighing 15 g is put into it. The temperature is raised to 120° C. over 15 to 20 minutes and kept for 30 minutes. The bath is then cooled to 60° C. over 10 to 15 minutes and the fabric is rinsed for 2 minutes in running cold water and subsequently dried for 20 minutes at 60° C. An excellent white effect of good lightfastness is obtained on the treated fabric.

Similarly good white effects are obtained by using a compound of the formula (104), (201) or (601) instead of the compound of the formula (702).

EXAMPLE 18

Polyester fabric is padded at room temperature with an aqueous dispersion containing 0.5 g/l of the compound of the formula (702) and 1 g of an adduct of about 8 moles of ethylene oxide with 1 mole of p-tert-octyl phenol. The pick-up is 60 to 70%. The fabric is dried at 100° C. and then heated for 30 seconds to 180° C. An excellent white effect of good lightfastness is obtained.

Similarly good white effects are obtained by using a compound of the formula (104), (201) or (601) instead of the compound of the formula (702).

EXAMPLE 19

Examples 17 and 18 are repeated, using an equivalent amount of one of the compounds of the formulae (301), (402), (501), (602) to (605), (803), (903), (1001), (1101), (1205), (1305), (1403), (1404), (1501), (1502) or (1601) to (1610) instead of the fluorescent whitening agent of the formula (702). Very good white effects are also obtained on polyester fabric.

EXAMPLE 20

Polyester fabric is padded at room temperature with an aqueous dispersion containg 0.5 g/l of a mixture consisting of 2 parts of the fluorescent whitening agent of the formula (702) and 1 part of the fluorescent whitening agent of the formula

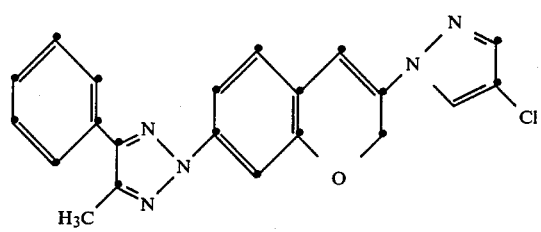

as well as 1 g of an adduct of about 8 moles of ethylene oxide and 1 mole of p-tert-octyl phenol. The pick-up is 60–70%. The fabric is dried at 100° C. and then heated for 30 seconds to 200° C. An excellent white effect of good lightfastness is obtained on the treated fabric.

EXAMPLE 21

Polyester fabric is treated as described in Example 20, using one of the fluorescent whitener mixtures A-I listed in the following Table II instead of the mixture used in Example 20.

TABLE II

| Mixture | Component 1 | Component 2 |
|---|---|---|
| A | 2 parts of the compound of the formula (702) | 1 part of the compound of the formula |

TABLE II-continued

| Mixture | Component 1 | Component 2 |
|---|---|---|
| B | 1 part of the compound of the formula (702) | 1 part of the compound of the formula<br><br>2,2'-dicyano-substituted distyrylbenzene: Ar(CN)–CH=CH–Ar–CH=CH–Ar(CN) |
| C | 1 part of the compound of the formula (702) | 2 parts of the compound of the formula<br><br>H₅C₂OOC—CH=CH—Ar—CH=CH—Ar—CH=CH—COOC₂H₅ |
| D | 1 part of the compound of the formula (702) | 1 part of the compound of the formula<br><br>N-methyl-4,5-diethoxy-naphthalimide derivative (with CH₃ on N, two C=O groups, H₅C₂O and OC₂H₅ substituents) |
| E | 3 parts of the compound of the formula (201) | 1 part of the compound of the formula<br><br>Cl—Ar—CH=CH—Ar—N(naphthotriazole) |
| F | 1 part of the compound of the formula (201) | 1 to 2 parts of the compound of the formula<br><br>H₃C-pyrazole-N–Ar–CH=CH–Ar (with O) |
| G | 1 part of the compound of the formula (201) | 1 part of the compound of the formula<br><br>biphenyl—CH=CH—Ar—C(=N)—O (dimethylbenzoxazole with two CH₃) |
| H | 1 part of the compound of the formula (201) | 9 parts of the compound of the formula<br><br>NC—CH=CH—Ar—CH=CH—Ar—CH=CH—CN |

TABLE II-continued

| Mixture | Component 1 | Component 2 |
|---|---|---|
| I | 1 part of the compound of the formula (104) | 1 part of a mixture of 99% of the compound of the formula 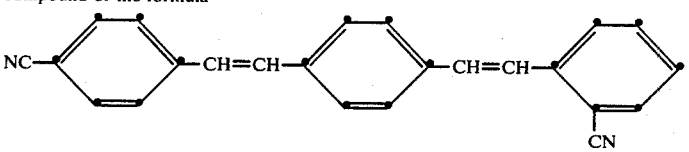 and 1% of the compound of the formula  |

An excellent white effect is obtained on the polyester fabric with each mixture.

EXAMPLE 22

Polyamide 66 woven tricot fabric is treated in a dyeing machine, at a liquor ratio of 1:20, with an aqueous bath which contains 0.2%, based on the weight of the fabric, of the compound of the formula (702), (601) or (201), 3 g/liter of a mixture of 60 parts by weight of sodium hydrosulfite and 40 parts by weight of sodium pyrophosphate, and 1 ml/liter 80% acetic acid. The bath is heated to 97° C. over 30 minutes, kept at this temperature for 30 minutes in running deionised water and dried with an iron at 180° C. A good white effect is obtained on the treated polyamide fabric with all three compounds.

Good white effects are also obtained on polyamide fabric using equivalent amounts of compounds of the formulae (104), (301), (402), (501), (602) to (605), (803), (903), (1001), (1101), (1205), (1305), (1403), (1404), (1501), (1502) or (1601) to (1600) in the above procedure instead of compounds of the formulae (702), (601) and (201).

An excellent white effect is also obtained on polyamide fabric by carrying out the procedure of this Example using the same amount of a mixture of 1 part of the compound of the formula (1001) and 1 part of the compound of the formula

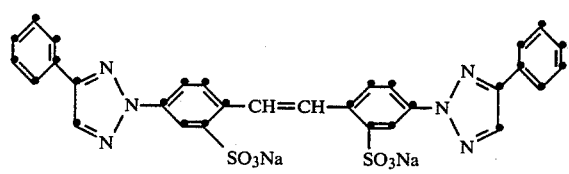

or of a mixture of 1 part of the compound of the formula (1001) and 1 part of the compound of the formula

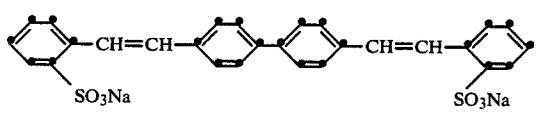

instead of the fluorescent whitening agents of the formulae (702), (601) and (201).

EXAMPLE 23

1 g of each of the fluorescent whitening agents of the formulae (201), (601) and (702) is dispersed in 1 liter of water. To 1.5 ml of this dispersion are added 100 ml of water containing 0.12 ml of 85% formic acid and 0.06 g of an alkyl polyglycol ether. This dispersion is heated to 60° C. and then a polyacrylonitrile fabric weighing 3 g is put into it. The temperature is raised over 10–15 minutes to 95°–97° C. and kept for 1 hour. The fabric is then rinsed for 2 minutes in running cold water and subsequently dried for 20 minutes at 60° C. A good white effect is obtained on the treated fabric.

EXAMPLE 24

Triacetate fabric is treated in a dyeing machine, at a liquor ratio of 1:20, with an aqueous bath which contains 0.1%, based on the weight of the fabric, of the compound of the formula (104), (201), (702), (1001) or (1205), and 1 g/liter of the condensation product of 35 moles of ethylene oxide and 1 mole of stearyl alcohol. The bath is then heated from 40° to 97° C. in the course of 30 minutes, kept at this temperature for 30 minutes, and then cooled to 30° C. over 15 minutes. The fabric is then rinsed in running deionised water and dried at 60° C. A good white effect is obtained on the treated triacetate fabric.

EXAMPLE 25

Acetate satin fabric is treated in a dyeing machine, at a liquor ratio of 1:20, with an aqueous bath which contains 0.1%, based on the weight of the fabric, of the compound of the formula (104), (201), (601) or (702), 1 g/liter of the condensation product of 35 moles of ethylene oxide and 1 mole of stearyl alcohol, and 0.5 ml/liter of 80% acetic acid. The bath is then heated from 40° to 80° C. over 30 minutes, kept at this temperature for 30 minutes, and then cooled to 20° C. over 15 minutes. The fabric is then rinsed in running deionised water and dried at 60° C. A good white effect is obtained on the treated acetate satin fabric.

EXAMPLE 26

1 kg of polyester granules of the ethylene glycol terephthalate type, containing 0.5% of $TiSO_2$ (anatase type), are mixed with 0.5 g of a compound of the formula (201), (601), (1501) or (702) in a rotary wheel mixer, and the treated granules are spun in an extruder at 280° C. to a multifilament. The excellent white effect obtained on the filaments has good lightfastness.

EXAMPLE 27

100 parts of polystyrene, containing about 1.5% of TiO$_2$ (rutile type), and 0.05 part of a compound of the formula (104), (301), (402) or (702) are mixed dry and the mixture is processed in an extruder at 180° C. to give whitened granules. The granules are moulded to small sheets in an injection moulding machine. The strong white effect obtained on the sheets has good lightfastness.

EXAMPLE 28

A homogeneous mixture of 65 parts of polyvinyl chloride (suspension type), 32 parts of dioctyl phthalate, 3 parts of an epoxidised soybean oil, 1.5 parts of a stabiliser, 0.5 part of a co-stabiliser, 5 parts of TiO$_2$ (rutile type) and 0.05 part of a compound of the formula (501), (1001), (1404) or (1601) is rolled on a calender at 150° C. to a film. The strong white effect obtained has good lightfastness.

What is claimed is:

1. A 4-styryl-4'vinylbiphenyl of the formula

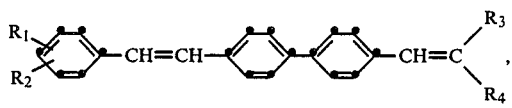

wherein each of R$_1$ and R$_2$ is hydrogen or a non-chromophoric substituent, or both together when ortho to each other complete a fused ring, R$_3$ is a second order non-chromophoric substituent and R$_4$ is hydrogen or alkyl or alkenyl, each unsubstituted or substituted by a non-chromophoric group.

2. A 4-styryl-4'-vinylbiphenyl of claim 1 wherein R$_1$ is hydrogen or halogen; alkyl, alkoxy or alkylsulfonyl, each unsubstituted or substituted by a non-chromophoric group; phenyl, phenylalkyl or phenylsulfonyl, phenoxy or phenylalkoxy, each unsubstituted or substituted by a non-chromophoric group; or is cyano, a group of the formula —COOY$_1$—, —CONY$_1$Y$_2$ or —SO$_2$NY$_1$Y$_2$, wherein each of Y$_1$ and Y$_2$ independently is hydrogen, alkenyl, propargyl, cycloalkyl containing 5 or 6 ring carbon atoms, or is alkyl, phenyl or phenylalkyl, each unsubstituted or substituted by a non-chromophoric group; or Y$_1$ and Y$_2$, together with the nitrogen atom to which they are attached, are a 5- or 6-membered saturated heterocyclic ring which can additionally contain 1 or 2 hetero-atoms as ring members and can also be substituted by an alkyl group; or wherein Y$_1$ is the group —COOY$_1$ can also additionally be a salt-forming cation; or R$_1$ is a group of the formula

wherein each of X$_1$ and Y independently of the other is halogen, alkyl, alkenyl, phenyl, phenylalkyl, hydroxy, alkoxy, phenylalkoxy, cycloalkoxy, phenoxy, amino, mono- or dialkylamino, phenyalkylamino, acylamino, phenylamino, cycloalkylamino, morpholino, piperidino or pyrrolidino; R$_2$ is hydrogen, halogen, or alkyl or alkoxy, each unsubstituted or substituted by a non-chromophoric group; or R$_1$ together with R$_2$ when ortho to each other are —CH=CH—CH=CH—, —O—CH$_2$—O— or —O—CH$_2$—CH$_2$—O—; R$_3$ is alkylsulfonyl, phenylsulfonyl, alkoxysulfonyl; cyano, trifluoromethyl, sulfo, a group of the formula —COOY$_1$, —CONY$_1$Y$_2$ or —SO$_2$NY$_1$Y$_2$, wherein Y$_1$ and Y$_2$ are as defined above; or is a group of the formula

wherein X$_1$ and Y are as defined above; and R$_4$ is hydrogen or alkyl which is unsubstituted or substituted by a non-chromophoric group.

3. A 4-styryl-4'-vinylbiphenyl of claim 2 wherein R$_1$ is hydrogen, halogen, C$_1$-C$_4$alkyl, C$_1$-C$_4$alkoxy, C$_1$-C$_4$alkylsulfonyl, cyano, or phenyl or phenylsulfonyl, each unsubstituted or substituted by one or more of chlorine, methyl and methoxy; or is a group of the formula —COOY$_1$, —CONY$_1$Y$_2$ or —SO$_2$NY$_1$Y$_2$, wherein Y$_1$ is hydrogen, C$_1$-C$_8$-alkyl, C$_3$-C$_4$alkenyl, cyclohexyl, C$_2$-C$_4$hydroxyalkyl, C$_3$-C$_6$alkoxyalkyl, a radical of the formula —CH$_2$CH$_2$O)$_n$(C$_1$-C$_4$alkyl), wherein n is an integer from 1 to 6, or is C$_6$-C$_9$phenoxyalkyl, C$_2$-C$_6$carboxyalkyl, C$_3$-C$_6$carbalkoxyalkyl, C$_2$-C$_5$cyanoalkyl, phenyl or benzyl, each unsubstituted or substituted by one or more of chlorine, methyl and methoxy, or is C$_3$-C$_7$dialkylaminoalkyl or phenethyl; Y$_2$ is hydrogen, C$_1$-C$_4$alkyl, C$_3$-C$_4$alkenyl or C$_2$-C$_4$hydroxyalkyl, or Y$_1$ and Y$_2$, together with the nitrogen atom to which they are attached, are a 5- or 6-membered saturated heterocyclic ring which can additionally contain a further nitrogen or oxygen atom as ring member and which can be substituted by 1 or 2 C$_1$-C$_4$alkyl groups; or wherein Y$_1$ in the group —COOY$_1$ can additionally be an alkali metal ion or an ammonium ion; or R$_1$ is a group of the formula

wherein each of X$_1$ and Y independently of the other is C$_1$-C$_4$alkyl, benzyl, phenyl which is unsubstituted or substituted by one or more of chlorine, methyl and methoxy; R$_2$ is hydrogen, halogen or C$_1$-C$_4$alkyl; R$_3$ is cyano, C$_1$-C$_4$alkylsulfonyl or a group of the formula —COOY$_1$, —CONY$_1$Y$_2$, SO$_2$NY$_1$Y$_2$ or

wherein Y$_1$, Y$_2$, X$_1$ and Y are as defined above; and R$_4$ is hydrogen or C$_1$-C$_4$alkyl.

4. A 4-styryl-4'-vinylbiphenyl of claim 3 wherein R$_1$ is halogen, C$_1$-C$_4$alkylsulfonyl, cyano or a group of the formula —COOY$_1$, wherein Y$_1$ is C$_1$-C$_8$alkyl, C$_3$-C$_4$alkenyl, C$_2$-C$_4$hydroxyalkyl, C$_3$-C$_6$alkoxyalkyl, a radical of the formula —CH$_2$CH$_2$—O)$_n$(C$_1$-C$_4$-alkyl), wherein n is an integer from 1 to 4, or is C$_2$-C$_6$carboxyalkyl, C$_3$-C$_6$carbalkoxyalkyl or C$_2$-C$_5$cyanoalkyl; or is a group of the formula

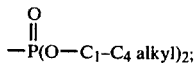

$R_2$ is hydrogen or halogen; $R_3$ is $C_1$-$C_4$alkylsulfonyl, cyano, a group of the formula

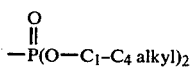

or a group of the formula —COOY$_1$, wherein Y$_1$ is as defined above, and R$_4$ is hydrogen or $C_1$-$C_4$alkyl.

5. A 4-styryl-4'-vinylbiphenyl of claim 4 wherein R$_1$ is $C_1$-$C_4$alkoxysulfonyl, cyano,

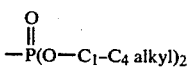

or —COOY$_1$, wherein Y$_1$, is $C_1$-$C_4$alkyl, $C_2$-$C_4$hydroxyalkyl, $C_3$-$C_6$alkoxyalkyl, (CH$_2$—CH$_2$—O)$_n$(-$C_1$-$C_4$alkyl), wherein n is an integer from 1 to 4, or is $C_3$-$C_6$carbalkoxyalkyl, $C_2$-$C_6$carboxyalkyl or $C_2$-$C_5$-cyanoalkyl; R$_2$ is hydrogen or halogen; R$_3$ is $C_1$-$C_4$alkylsulfonyl, cyano,

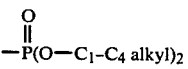

or —COOY$_1$, wherein Y$_1$ is as defined above; and R$_4$ is hydrogen.

6. A 4-styryl-4'-vinylbiphenyl of claim 5, wherein R$_1$ is cyano or —COOY$_1$, wherein Y$_1$ is $C_1$-$C_4$alkyl, $C_2$-$C_4$hydroxyalkyl, $C_3$-$C_6$alkoxyalkyl or —CH$_2$—CH$_2$—O)$_n$($C_1$-$C_4$alkyl), wherein n is an integer from 1 to 4, R$_3$ is cyano or —COOY$_1$, wherein Y$_1$ is as defined above, and R$_2$ is hydrogen or chlorine.

7. A 4-styryl-4'-vinylbiphenyl of claim 5, wherein R$_1$ is cyano, R$_2$ is hydrogen, and R$_3$ is cyano or —COOY$_1$, in which Y$_1$ is $C_1$-$C_4$alkyl, $C_2$-$C_4$hydroxyalkyl, $C_3$-$C_6$alkoxyalkyl or —CH$_2$—CH$_2$—O)$_n$($C_1$-$C_4$alkyl), wherein n is an integer from 1 to 4.

8. The 4-styryl-4'-vinylbiphenyl of claim 7 of the formula

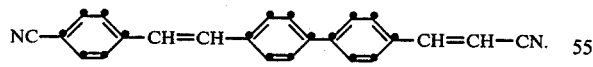

9. A process for the production of a 4-styryl-4'-vinylbiphenyl of claim 1, which process comprises reacting a biphenyl-4,4'-dialdehyde of the formula

with a compound of the formula

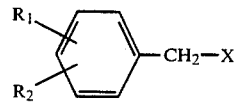

to give an aldehyde of the formula

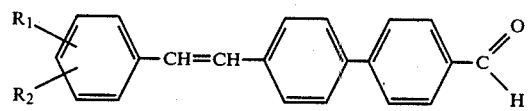

and subsequently reacting this aldehyde with a compound of the formula

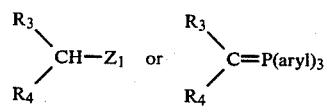

to give a compound of claim 1, in which formulae above R$_1$, R$_2$, R$_3$ and R$_4$ are as defined in claim 1, and X and Z$_1$ are the same or different and each independently of the other is hydrogen, a radical of the formula —COOZ, wherein Z is hydrogen or alkyl,

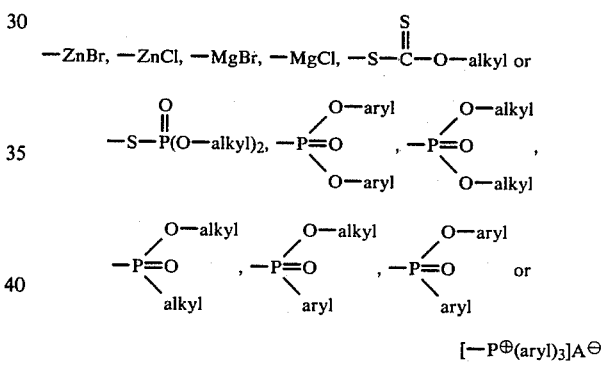

$[—P^{\oplus}(aryl)_3]A^{\ominus}$ wherein $A^{\ominus}$ is a monovalent colorless anion.

10. A process according to claim 9, wherein each of X and Z$_1$ independently of the other is a group of the formula

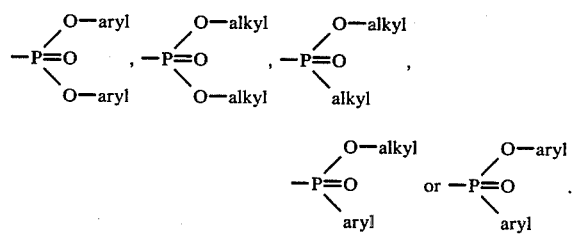

11. A process for the production of a 4-styryl-4'-vinylbiphenyl of claim 1, which process comprises reacting a biphenyl-4,4'-dialdehyde of the formula

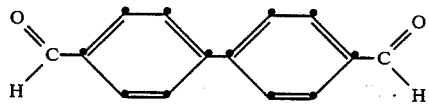

with a compound of the formula $$\begin{matrix} R_3 \\ R_4 \end{matrix} CH-Z_1 \quad \text{or} \quad \begin{matrix} R_3 \\ R_4 \end{matrix} C=P(aryl)_3$$

to give an aldehyde of the formula $$\underset{H}{\overset{O}{\|}}C-\text{[biphenyl]}-CH=C\begin{matrix} R_3 \\ R_4 \end{matrix}$$

and subsequently reacting this aldehyde with a compound of the formula $$\begin{matrix} R_1 \\ R_2 \end{matrix}\text{[phenyl]}-CH_2-X$$

to give a compound of claim 1, in which formulae above $R_1$, $R_2$, $R_3$ and $R_4$ are as defined in claim 1, and X and $Z_1$ are the same or different and each independently of the other is hydrogen or a radical of the formula —COOZ, wherein Z is hydrogen or alkyl, $$-ZnBr, -ZnCl, -MgBr, -MgCl, -S-\overset{\overset{S}{\|}}{C}-O-\text{alkyl or}$$

$$-S-\overset{\overset{O}{\|}}{P}(O-\text{alkyl})_2, -P\underset{O-\text{aryl}}{\overset{O-\text{aryl}}{=}}O, -P\underset{O-\text{alkyl}}{\overset{O-\text{alkyl}}{=}}O,$$

$$-P\underset{\text{alkyl}}{\overset{O-\text{alkyl}}{=}}O, -P\underset{\text{aryl}}{\overset{O-\text{alkyl}}{=}}O, -P\underset{\text{aryl}}{\overset{O-\text{aryl}}{=}}O \quad \text{or}$$

$$[-P^{\oplus}(\text{aryl})_3]A^{\ominus}$$

wherein $A^{\ominus}$ is a monovalent colorless anion.

12. A process of any of claims 9 to 11, wherein the reaction of the biphenyl-4,4′-dialdehyde with a compound of the formula $$\begin{matrix} R_1 \\ R_2 \end{matrix}\text{[phenyl]}-CH_2-X, \quad \begin{matrix} R_3 \\ R_4 \end{matrix} CH-Z_1 \text{ or } \begin{matrix} R_3 \\ R_4 \end{matrix} C=P(aryl)_3$$

is carried out in a solvent in which the resultant monoaldehyde is sparingly soluble and from which it crystallizes out.

13. A process of any one of claims 9 to 11, wherein the reaction of the biphenyl-4,4′-dialdehyde with a compound of the formula $$\begin{matrix} R_1 \\ R_2 \end{matrix}\text{[phenyl]}-CH_2X, \quad \begin{matrix} R_3 \\ R_4 \end{matrix} CH-Z_1 \text{ or } \begin{matrix} R_3 \\ R_4 \end{matrix} C=P(aryl)_3$$

is carried out in the presence of an alkali condensing agent, in the temperature range of 0° to 50° C.

14. A process of any one of claims 9 to 11, wherein the monoaldehyde obtained in the first step is further reacted without being isolated.

15. A process of any one of claims 9 to 11, wherein the monoaldehyde obtained in the first step is isolated and then without purification further reacted in a solvent in which the monoaldehyde is soluble.

16. A process of claim 15, wherein the reaction of the monoaldehyde obtained in the first step with a compound of the formula $$\begin{matrix} R_1 \\ R_2 \end{matrix}\text{[phenyl]}-CH_2-X, \quad \begin{matrix} R_3 \\ R_4 \end{matrix} CH-Z_1 \text{ or } \begin{matrix} R_3 \\ R_4 \end{matrix} C=P(aryl)_3$$

is carried out in the presence of an alkali metal alcoholate, in the temperature range of 20° to 100° C.

17. A composition for whitening organic material of high molecular weight which contains one or more compounds of claim 1, with conventional formulation additives.

18. A composition according to claim 17 which contains an additional fluorescent whitening agent which gives a greenish to bluish hue on the reacted substrate.

19. A composition according to claim 18 wherein the additional fluorescent whitening agent is selected from the group consisting of the bis-styrylbenzenes, benzoxazolylstilbenes, 4,4′-divinylstilbenes, naphthalimides, 4,4′-bis-styrylbiphenyls, 4,4′-bis-triazolylstilbenes, bisbenzoxazolylthiophenes, naphthotriazolylstilbenes and coumarines.

20. A composition according to claim 19 wherein the fluorescent whitener consists of 10 to 90%, of the first fluorescent whitening agent, and 90 to 1% of the additional fluorescent whitening agent.

21. A process for whitening a natural, regenerated or synthetic organic substrate of high molecular weight, which process comprises incorporating in or applying to said substrate a compound of claim 1.

22. A process according to claim 21 for whitening a polyester substrate.

23. A process according to either of claims 21 or 22 which comprises incorporating in or applying to the substrate to be whitened 0.001 to 2%, of fluorescent whitening agent or of a mixture of fluorescent whitening agent, based on the weight of said substrate.

24. Organic material of high molecular weight, containing 0.001 to 2%, of a fluorescent whitening agent of claim 1.

* * * * *